US009814430B1

(12) United States Patent
Berme et al.

(10) Patent No.: US 9,814,430 B1
(45) Date of Patent: Nov. 14, 2017

(54) SYSTEM AND METHOD FOR MEASURING EYE MOVEMENT AND/OR EYE POSITION AND POSTURAL SWAY OF A SUBJECT

(71) Applicant: Bertec Corporation, Columbus, OH (US)

(72) Inventors: Necip Berme, Worthington, OH (US); Kamran Barin, Columbus, OH (US)

(73) Assignee: Bertec Corporation, Columbus, OH (US)

( * ) Notice: Subject to any disclaimer, the term of this patent is extended or adjusted under 35 U.S.C. 154(b) by 0 days.

(21) Appl. No.: 14/689,632

(22) Filed: Apr. 17, 2015

(51) Int. Cl.
| | |
|---|---|
| *A61B 5/00* | (2006.01) |
| *G06F 19/00* | (2011.01) |
| *A61B 3/113* | (2006.01) |
| *A61B 5/11* | (2006.01) |
| *A61B 8/10* | (2006.01) |
| *A61B 5/0496* | (2006.01) |
| *A61B 8/00* | (2006.01) |

(52) U.S. Cl.
CPC ............ *A61B 5/7275* (2013.01); *A61B 3/113* (2013.01); *A61B 5/0059* (2013.01); *A61B 5/0077* (2013.01); *A61B 5/0496* (2013.01); *A61B 5/11* (2013.01); *A61B 5/4023* (2013.01); *A61B 5/6803* (2013.01); *A61B 5/742* (2013.01); *A61B 8/10* (2013.01)

(58) Field of Classification Search
CPC ............................ A61B 5/1101; A61B 5/1122
See application file for complete search history.

(56) References Cited

U.S. PATENT DOCUMENTS

| | | | |
|---|---|---|---|
| 6,038,488 | A | 3/2000 | Barnes et al. |
| 6,113,237 | A | 9/2000 | Ober et al. |
| 6,152,564 | A | 11/2000 | Ober et al. |
| 6,295,878 | B1 | 10/2001 | Berme |
| 6,354,155 | B1 | 3/2002 | Berme |

(Continued)

FOREIGN PATENT DOCUMENTS

WO    WO 2014138414 A1 *  9/2014   ......... A61B 5/04842

OTHER PUBLICATIONS

BalanceCheck Screener—Protocol Guide, Bertec Corporation, Version 1.1.0, last updated Mar. 2012.

(Continued)

*Primary Examiner* — William Thomson
*Assistant Examiner* — Amanda Steinberg
(74) *Attorney, Agent, or Firm* — The Law Office of Patrick F. O'Reilly, III, LLC

(57) ABSTRACT

A system and method for measuring eye movement and/or eye position and postural sway of a subject is disclosed herein. The system generally includes an eye movement tracking device, a postural sway detection device, and a data processing device operatively coupled to the eye movement tracking device and the postural sway detection device. During the execution of the method, the eye movement and/or eye position of the subject is measured using the eye movement tracking device, and the postural sway of the subject is measured using the postural sway detection device. A method for determining a gaze direction of a subject during a balance test and/or concussion screening test, and a method for assessment of a medical condition of a subject are also disclosed herein.

13 Claims, 17 Drawing Sheets

(56) References Cited

U.S. PATENT DOCUMENTS

| | | | |
|---|---|---|---|
| 6,389,883 B1* | 5/2002 | Berme | A61B 5/4023 73/65.01 |
| 6,743,022 B1* | 6/2004 | Sarel | 434/236 |
| 6,936,016 B2 | 8/2005 | Berme et al. | |
| 8,181,541 B2 | 5/2012 | Berme | |
| 8,315,822 B2 | 11/2012 | Berme et al. | |
| 8,315,823 B2 | 11/2012 | Berme et al. | |
| D689,388 S | 9/2013 | Berme | |
| D689,389 S | 9/2013 | Berme | |
| 8,543,540 B1 | 9/2013 | Wilson et al. | |
| 8,544,347 B1 | 10/2013 | Berme | |
| 8,643,669 B1 | 2/2014 | Wilson et al. | |
| 8,700,569 B1 | 4/2014 | Wilson et al. | |
| 8,704,855 B1 | 4/2014 | Berme et al. | |
| 8,764,532 B1* | 7/2014 | Berme | A61B 5/742 434/258 |
| 8,845,096 B1* | 9/2014 | Cohen et al. | 351/203 |
| 8,847,989 B1 | 9/2014 | Berme et al. | |
| D715,669 S | 10/2014 | Berme | |
| 8,902,249 B1 | 12/2014 | Wilson et al. | |
| 8,915,149 B1 | 12/2014 | Berme | |
| 9,032,817 B2 | 5/2015 | Berme et al. | |
| 9,043,278 B1 | 5/2015 | Wilson et al. | |
| 9,066,667 B1 | 6/2015 | Berme et al. | |
| 2002/0011250 A1* | 1/2002 | Stewart | A61B 5/00 128/898 |
| 2003/0216656 A1 | 11/2003 | Berme et al. | |
| 2005/0240253 A1* | 10/2005 | Tyler | A61B 5/0492 607/134 |
| 2006/0161218 A1* | 7/2006 | Danilov | A61B 5/0492 607/45 |
| 2007/0027369 A1* | 2/2007 | Pagnacco et al. | 600/301 |
| 2007/0299362 A1* | 12/2007 | Epley et al. | 600/559 |
| 2008/0228110 A1 | 9/2008 | Berme | |
| 2009/0240172 A1* | 9/2009 | Fernandez Tournier et al. | 600/595 |
| 2010/0216104 A1* | 8/2010 | Reichow et al. | 434/258 |
| 2010/0331721 A1* | 12/2010 | Epley | 600/552 |
| 2011/0007275 A1* | 1/2011 | Yoo et al. | 351/209 |
| 2011/0208444 A1* | 8/2011 | Solinsky | A61B 5/112 702/41 |
| 2011/0277562 A1 | 11/2011 | Berme | |
| 2012/0123232 A1* | 5/2012 | Najarian | A61B 5/0022 600/345 |
| 2012/0266648 A1 | 10/2012 | Berme et al. | |
| 2012/0271565 A1 | 10/2012 | Berme et al. | |
| 2012/0310117 A1* | 12/2012 | Teicher | A61B 5/1124 600/595 |
| 2013/0066424 A1* | 3/2013 | Hessler et al. | 623/10 |
| 2013/0278899 A1* | 10/2013 | Waldorf | A61B 3/032 351/209 |
| 2014/0058241 A1* | 2/2014 | Apparies et al. | 600/383 |
| 2014/0081177 A1* | 3/2014 | Eguibar et al. | 600/595 |
| 2014/0255888 A1* | 9/2014 | Stack | 434/236 |
| 2015/0096387 A1 | 4/2015 | Berme et al. | |
| 2015/0169953 A1* | 6/2015 | Border | G06K 9/00604 348/78 |
| 2016/0015289 A1* | 1/2016 | Simon | A61B 5/04842 600/301 |
| 2016/0278684 A1* | 9/2016 | Kozloski | A61B 3/0025 |

OTHER PUBLICATIONS

BalanceCheck Trainer—Protocol Guide, Bertec Corporation, Version 1.1.0, last updated Mar. 2012.

Bertec Workbook—Program Documentation, Bertec Corporation, Version 1.1.0, last updated Mar. 2012.

Digital Acquire 4—Program Documentation, Bertec Corporation, Version 4.0.11, last updated Jul. 2012.

Bertec Force Plates, Bertec Corporation, Version 1.0.0, last updated Mar. 2012.

Wrap Augmented Reality Glasses, Vuzix Website, Web page <http://www.vuzix.com/augmented-reality/products_wrap1200ar.html>, 2 pages, dated Jul. 2, 2013, retrieved from Internet Archive Wayback Machine <https://web.archive.org/web/20130702182224/http://www.vuzix.com/augmented-reality/products_wrap1200ar.html#description> on Oct. 15, 2014.

Eye Tracker with Scene Camera, SR Research Website, Web page <http://www.sr-research.com/EL_II_scam.html>, 1 page, dated Apr. 22, 2012, retrieved from Internet Archive Wayback Machine <https://web.archive.org/web/20120422195146/http://www.sr-research.com/EL_II_scam.html> on Oct. 15, 2014.

* cited by examiner

Head Moving Without Torso and Target Moving

SYSTEM AND METHOD FOR MEASURING EYE MOVEMENT AND/OR EYE POSITION AND POSTURAL SWAY OF A SUBJECT

CROSS-REFERENCE TO RELATED APPLICATIONS

Not Applicable.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to the combined measurement of eye movement and postural sway of a subject or patient. More particularly, the invention relates to a system and method for measuring eye movement and/or eye position and postural sway of a subject.

2. Background

Patients with damage to the inner ear balance system suffer from lack of head-eye coordination. That means, when these patients move the head, their vision becomes blurry and their balance function deteriorates accordingly. As one example of a cause, damage to the inner ear balance system may occur as a result of the patient sustaining a traumatic brain injury (TBI) or concussion.

These patients with damaged inner ear balance systems are often given head-eye coordination exercises to regain function. However, with the conventional rehabilitation methods currently used, there is no way to quantify the head, eye, and postural movements during such exercises in order to determine if the patients are regaining the normal functionality of their inner ear balance systems.

What is needed, therefore, is a system and method for measuring eye movement and/or eye position and postural sway of a subject that provides quantification of head, eye, and postural movements during head-eye coordination exercises. Moreover, a system and method for measuring eye movement and/or eye position and postural sway of a subject or patient is needed that enables a patient's functional status to be objectively documented before, during, after therapy. Furthermore, a need exists for a system and method for measuring eye movement and/or eye position and postural sway of a subject or patient that enables a medical condition to be assessed (e.g., a traumatic brain injury (TBI) or concussion) so that the proper treatment procedures can be implemented.

BRIEF SUMMARY OF THE INVENTION

Accordingly, the present invention is directed to a system and method for measuring eye movement and/or eye position and postural sway of a subject that substantially obviates one or more problems resulting from the limitations and deficiencies of the related art.

In accordance with one aspect of the present invention, there is provided a method for concurrently measuring the eye movement and/or eye position and postural sway of a subject. The method includes the steps of: (i) providing an eye movement tracking device configured to track eye movement and/or eye position of the subject while the subject performs a balance test and/or a concussion screening test, the eye movement tracking device being configured to output one or more first signals that are representative of the detected eye movement and/or eye position of the subject; (ii) providing a postural sway detection device, the postural sway detection device configured to detect a postural sway of the subject while the subject performs the balance test and/or the concussion screening test, the postural sway detection device being configured to output one or more second signals that are representative of the detected postural sway of the subject; (iii) providing a data processing device operatively coupled to the eye movement tracking device and the postural sway detection device, the data processing device configured to receive the one or more first signals that are representative of the detected eye movement and/or eye position of the subject and the one or more second signals that are representative of the detected postural sway of the subject, the data processing device further configured to determine the eye movement and/or eye position of the subject using the one or more first signals and the postural sway of the subject using the one or more second signals; (iv) positioning the subject in an upright position on a surface; (v) measuring the eye movement and/or eye position of the subject using the eye movement tracking device, and outputting the one or more first signals that are representative of the detected eye movement and/or eye position of the subject from the eye movement tracking device; (vi) measuring the postural sway of the subject using the postural sway detection device while measuring the eye movement and/or eye position of the subject, and outputting the one or more second signals that are representative of the postural sway of the subject from the postural sway detection device; (vii) determining, by using the data processing device, eye movement and/or eye position data for the subject from the one or more first signals output by the eye movement tracking device; and (viii) determining, by using the data processing device, postural sway data for the subject from the one or more second signals output by the postural sway detection device.

In a further embodiment of this aspect of the present invention, the eye movement tracking device comprises at least one of the following: (i) a video camera, (ii) an infrared sensor, (iii) an ultrasonic sensor, and (iv) an electrooculographic sensor. Also, in this further embodiment, the step of measuring the eye movement and/or eye position of the subject using the eye movement tracking device further comprises measuring the eye movement and/or eye position of the subject using at least one of: (i) the video camera, (ii) the infrared sensor, (iii) the ultrasonic sensor, and (iv) the electrooculographic sensor.

In yet a further embodiment, the postural sway detection device comprises at least one of the following: (i) a force or balance plate, (ii) one or more inertial measurement units, (iii) an optical motion capture device, and (iv) an infrared motion capture device. Also, in this further embodiment, the step of measuring the postural sway of the subject using the eye movement tracking device further comprises measuring the postural sway of the subject using at least one of: (i) a force or balance plate, (ii) one or more inertial measurement units, (iii) an optical motion capture device, and (iv) an infrared motion capture device.

In still a further embodiment, the method further comprises the steps of: (ix) determining, by using the data processing device, a first numerical score for the subject based upon the eye movement and/or eye position data determined for the subject; (x) determining, by using the data processing device, a second numerical score for the subject based upon the postural sway data determined for the subject; and (xi) combining, by using the data processing device, the first numerical score with the second numerical score to obtain an overall combined sway and eye movement score for the subject.

In yet a further embodiment, the method further comprises the steps of: (ix) determining, by using the data processing device, one or more eye movement deviation values based upon the eye movement and/or eye position data determined for the subject, the one or more eye movement deviation values quantifying instances during the balance test and/or the concussion screening test where the subject is unable to follow a particular target; (x) determining, by using the data processing device, a balance sway score for the subject based upon the postural sway data determined for the subject; and (xi) computing, by using the data processing device, an adjusted balance sway score for the subject by increasing the balance sway score determined for the subject by a numerical factor proportionate to the one or more eye movement deviation values.

In accordance with another aspect of the present invention, there is provided a method for determining a gaze direction of a subject during a balance test and/or concussion screening test. The method comprising the steps of: (i) providing an eye movement tracking device configured to track eye movement and/or eye position of the subject while the subject performs the balance test and/or the concussion screening test, the eye movement tracking device being configured to output one or more first signals that are representative of the detected eye movement and/or eye position of the subject; (ii) providing a head position detection device, the head position detection device configured to detect a position of a head of a subject and output one or more second signals that are representative of the detected position of the head of the subject; (iii) providing at least one limb position detection device, the at least one limb position detection device configured to detect a position of one or more limbs of a subject and output one or more third signals that are representative of the detected position of the one or more limbs of the subject; (iv) providing a data processing device operatively coupled to the eye movement tracking device, the head position detection device, and the at least one limb position detection device, the data processing device configured to receive the one or more first signals that are representative of the detected eye movement and/or eye position of the subject, the one or more second signals that are representative of the detected position of the head of the subject, and the one or more third signals that are representative of the detected position of the one or more limbs of the subject, the data processing device further configured to determine one or more gaze directions of the subject using the one or more first signals and the one or more second signals, and to determine a position of one or more limbs of the subject using the one or more third signals; (v) positioning the eye movement tracking device on the subject or on an object proximate to the subject; (vi) positioning the head position detection device on a head of the subject or on an object proximate to the head of the subject; (vii) positioning the at least one limb position detection device on one or more limbs of the subject; (viii) measuring eye movement and/or eye position of the subject using the eye movement tracking device and head position of the subject using the head position detection device while at least one of the one or more limbs of the subject and the head of the subject are displaced by the subject, and outputting the one or more first signals that are representative of the detected eye movement and/or eye position of the subject from the eye movement tracking device and outputting the one or more second signals that are representative of the detected position of the head of the subject from the head position detection device; (ix) determining, by using the data processing device, one or more gaze directions of the subject from the one or more first signals output by the eye movement tracking device and the one or more second signals output by the head position detection device; (x) determining, by using the data processing device, a position of one or more limbs of the subject from the one or more third signals output by the at least one limb position detection device; and (xi) determining, by using the data processing device, whether the one or more gaze directions of the subject determined from the one or more first signals of the eye movement tracking device and the one or more second signals of the head position detection device correspond to a direction in which the one or limbs of the subject are pointed while the at least one of the one or more limbs of the subject and the head of the subject are displaced by the subject during a performance of the balance test and/or the concussion screening test.

In a further embodiment of this aspect of the present invention, the step of positioning the eye movement tracking device on the subject or on an object proximate to the subject further comprises positioning the eye movement tracking device on a graspable object held in one or more hands of the subject during the performance of the balance test and/or the concussion screening test.

In yet a further embodiment, the step of positioning the eye movement tracking device on the subject or on an object proximate to the subject further comprises positioning the movement tracking device on glasses or goggles worn by the subject during the performance of the balance test and/or the concussion screening test.

In still a further embodiment, the step of measuring the eye movement and/or eye position, and the head position of the subject while at least one of the one or more limbs of the subject and the head of the subject are displaced by the subject further comprises measuring the eye movement, the eye position, and the head position of the subject while the head of the subject is rotated, the one or more limbs of the subject are stationary, and a gaze orientation of the subject is maintained on a portion of the one or more limbs of the subject.

In yet a further embodiment, the step of measuring the eye movement and/or eye position, and the head position of the subject while at least one of the one or more limbs of the subject and the head of the subject are displaced by the subject further comprises measuring the eye movement, the eye position, and the head position of the subject while the one or more limbs of the subject are rotated, the head of the subject is rotated generally in sync with the one or more limbs, and a gaze orientation of the subject is maintained on a portion of the one or more limbs of the subject during rotation of the one or more limbs.

In still a further embodiment, the head position detection device comprises one or more inertial measurement units, and the step of measuring the eye movement and/or eye position, and the head position of the subject further comprises measuring the head position of the subject with the at least one inertial measurement unit.

In yet a further embodiment, the method further comprises the steps of: (xii) providing a force measurement assembly configured to receive the subject, the force measurement assembly including a surface for receiving at least one portion of the body of the subject; and at least one force transducer, the at least one force transducer configured to sense one or more measured quantities and output one or more fourth signals that are representative of forces and/or moments being applied to the surface of the force measurement assembly by the subject; (xiii) positioning the subject on the surface of the force measurement assembly in an upright position; (xiv) sensing, by utilizing the at least one force transducer, one or more measured quantities that are representative of forces and/or moments being applied to the surface of the force measurement assembly by the subject and outputting one or more fourth signals representative thereof while at least one of the one or more limbs of the subject and the head of the subject are displaced by the subject; (xv) converting, by using the data processing device, the one or more fourth signals that are representative of the forces and/or moments being applied to the surface of the force measurement assembly by the subject into one or more load output values; and (xvi) computing, by using the data processing device, one or more numerical values that are indicative of a postural stability of a subject by using the one or more load output values while at least one of the one or more limbs of the subject and the head of the subject are displaced by the subject.

In accordance with yet another aspect of the present invention, there is provided a method for assessment of a medical condition of a subject. The method comprising the steps of: (i) providing a measurement assembly configured to receive a subject thereon, the measurement assembly including a surface for receiving at least one portion of a body of a subject, and at least one measurement device, the at least one measurement device configured to sense one or more measured quantities and output one or more first signals that are generated based upon the subject's contact with the surface; (ii) providing an eye movement tracking device configured to track eye movement and/or eye position of the subject while the subject performs one or more tasks and/or tests, the eye movement tracking device being configured to output one or more second signals that are representative of the detected eye movement and/or eye position of the subject; (iii) providing a data processing device operatively coupled to the at least one measurement device of the measurement assembly and the eye movement tracking device; (iv) positioning the subject on the measurement assembly; (v) instructing the subject to perform a first task, which involves one or more changes in eye position by the subject, and a second task, which comprises one or more detectable movements on the surface of the measurement assembly; (vi) sensing, by utilizing the at least one measurement device, one or more measured quantities and outputting one or more first signals that are generated based upon the one or more detectable movements on the surface of the measurement assembly; (vii) measuring the eye movement and/or eye position of the subject using the eye movement tracking device while the subject performs the first task, and outputting the one or more second signals that are representative of the detected eye movement and/or eye position of the subject from the eye movement tracking device; (viii) receiving, at the data processing device, the one or more first signals that are generated based upon the one or more detectable movements of the subject on the surface of the measurement assembly, and the one or more second signals that are representative of the detected eye movement and/or eye position of the subject; (ix) computing, by using the data processing device, one or more numerical values from the one or more first signals outputted by the at least one measurement device; (x) determining, by using the data processing device, one or more changes in eye position of the subject from the one or more second signals output by the eye movement tracking device; (xi) quantitatively determining, by using the data processing device, a subject's performance during the first and second tasks, the assessment of the subject's performance of the first task being based at least partially upon the one or more changes in eye position of the subject, the assessment of the subject's performance of the second task being based at least partially upon the one or more numerical values, the subject's performance of the first task being quantitatively expressed in terms of one or more first performance values and the subject's performance of the second task being quantitatively expressed in terms of one or more second performance values; and (xii) assessing a medical condition of the subject by using at least one of the one or more first and second performance values.

In a further embodiment of this aspect of the present invention, the first task comprises a neurocognitive task and the second task comprises a motor or muscular task.

In yet a further embodiment, the neurocognitive task comprises reading one or more passages on a visual display device, and wherein the motor or muscular task comprises maintaining a substantially stationary, upright position on the surface of the measurement assembly.

In still a further embodiment, the one or more first performance parameters for assessing the subject's performance of the first task comprise one or more of the following: (i) an eye pursuit performance parameter specifying an amount that one or more eyes of the subject lag behind an intended target, (ii) an eye velocity of one or more eyes of the subject, (iii) an eye pursuit performance ratio of eye velocity to target velocity for the subject, (iii) an accuracy parameter specifying an accuracy of one or more eyes of the subject, and (iv) an eye latency parameter specifying a time for the subject to initiate eye movements.

In yet a further embodiment, the one or more second performance parameters for assessing the subject's performance of the second task comprise one or more of the following: (i) a maximum sway range of the center of pressure of a force vector applied by the subject on the measurement assembly, (ii) a maximum sway range of the center of gravity of the subject, and (iii) a confidence area for a path of the subject's center of pressure.

In still a further embodiment, the step of assessing the medical condition of the subject by using at least one of the one or more first and second performance values comprises assessing one or more of the following medical conditions: (i) a traumatic brain injury or concussion, (ii) a neurological disorder or disease, and (iii) a muscular disorder or disease.

In yet a further embodiment, the method further comprises the step of: (xiii) combining, by using the data processing device, the first performance value with the second performance value to obtain an overall combined score for assessing the medical condition of the subject.

In still a further embodiment, the measurement assembly comprises one of a force measurement assembly, a pressure measurement assembly, and a contact or timing measurement assembly; and the at least one measurement device comprises one of a force transducer, a pressure transducer, and a contact or timing switch.

It is to be understood that the foregoing summary and the following detailed description of the present invention are merely exemplary and explanatory in nature. As such, the foregoing summary and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

Figure 1:
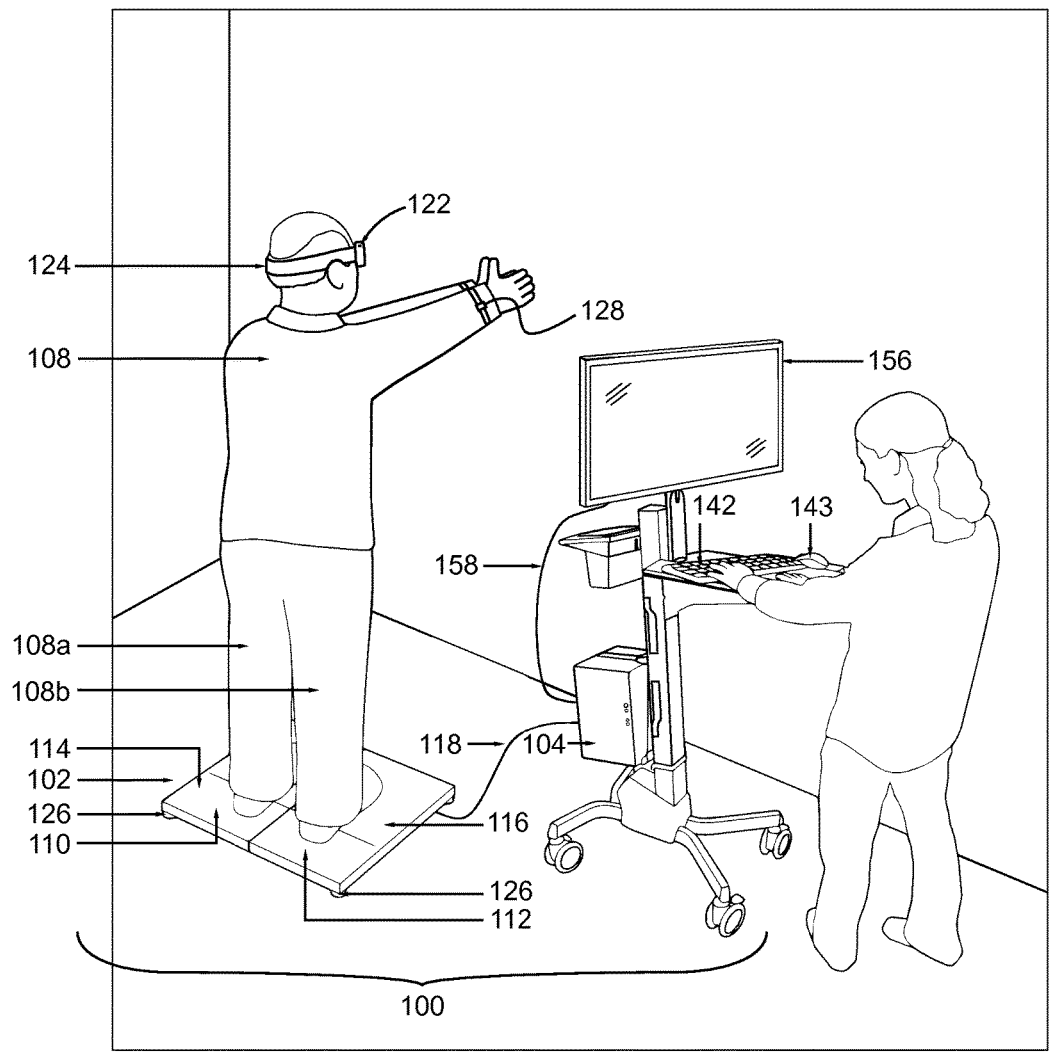
FIG. 1 is a diagrammatic perspective view of a system for measuring postural sway, eye movement and/or eye position, and gaze direction, according to a first embodiment of the invention, wherein the postural sway detection device is in the form of a force plate.

An exemplary embodiment of a system for measuring postural sway, eye movement and/or eye position, and gaze direction is seen generally at 100 in FIG. 1. The system 100 in FIG. 1 generally comprises a force measurement assembly 102 that is operatively coupled to a data acquisition/data processing device 104 (i.e., a computing device that is capable of collecting, storing, and processing data), which in turn, is operatively coupled to an eye movement and eye position tracking device 124, and an operator visual display device 156. As illustrated in FIG. 1, the force measurement assembly 102 is configured to receive a subject 108 thereon, and is capable of measuring the forces and/or moments applied to its measurement surfaces 114, 116 by the subject 108.

As shown in FIG. 1, the data acquisition/data processing device 104 includes a plurality of user input devices 142, 143 connected thereto. Preferably, the user input devices 142, 143 comprise a keyboard 142 and a mouse 143. In addition, the operator visual display device 156 may also serve as a user input device if it is provided with touch screen capabilities. While a desktop type computing system is depicted in FIG. 1, one of ordinary of skill in the art will appreciate that another type of data acquisition/data processing device 104 can be substituted for the desktop computing system such as, but not limited to, a laptop or a palmtop computing device (i.e., a PDA).

As illustrated in FIG. 1, force measurement assembly 102 is operatively coupled to the data acquisition/data processing device 104 by virtue of an electrical cable 118. In one embodiment of the invention, the electrical cable 118 is used for data transmission, as well as for providing power to the force measurement assembly 102. Various types of data transmission cables can be used for cable 118. For example, the cable 118 can be a Universal Serial Bus (USB) cable or an Ethernet cable. Preferably, the electrical cable 118 contains a plurality of electrical wires bundled together, with at least one wire being used for power and at least another wire being used for transmitting data. The bundling of the power and data transmission wires into a single electrical cable 118 advantageously creates a simpler and more efficient design. In addition, it enhances the safety of the testing environment when human subjects are being tested on the force measurement assembly 102. However, it is to be understood that the force measurement assembly 102 can be operatively coupled to the data acquisition/data processing device 104 using other signal transmission means, such as a wireless data transmission system. If a wireless data transmission system is employed, it is preferable to provide the force measurement assembly 102 with a separate power supply in the form of an internal power supply or a dedicated external power supply.

Referring again to FIG. 1, it can be seen that the force measurement assembly 102 of the illustrated embodiment is in the form of a dual force plate assembly. The dual force plate assembly includes a first plate component 110, a second plate component 112, at least one force transducer associated with the first plate component 110, and at least one force transducer associated with the second plate component 112. In the illustrated embodiment, a subject 108 stands in an upright position on the force measurement assembly 102 and each foot of the subject 108 is placed on the top surfaces 114, 116 of a respective plate component 110, 112 (i.e., one foot on the top surface 114 of the first plate component 110 and the other foot on the top surface 116 of the second plate component 112). The at least one force transducer associated with the first plate component 110 is configured to sense one or more measured quantities and output one or more first signals that are representative of forces and/or moments being applied to its measurement surface 114 by the left foot/leg 108a of the subject 108, whereas the at least one force transducer associated with the second plate component 112 is configured to sense one or more measured quantities and output one or more second signals that are representative of forces and/or moments being applied to its measurement surface 116 by the right foot/leg 108b of subject 108.

Figure 4:
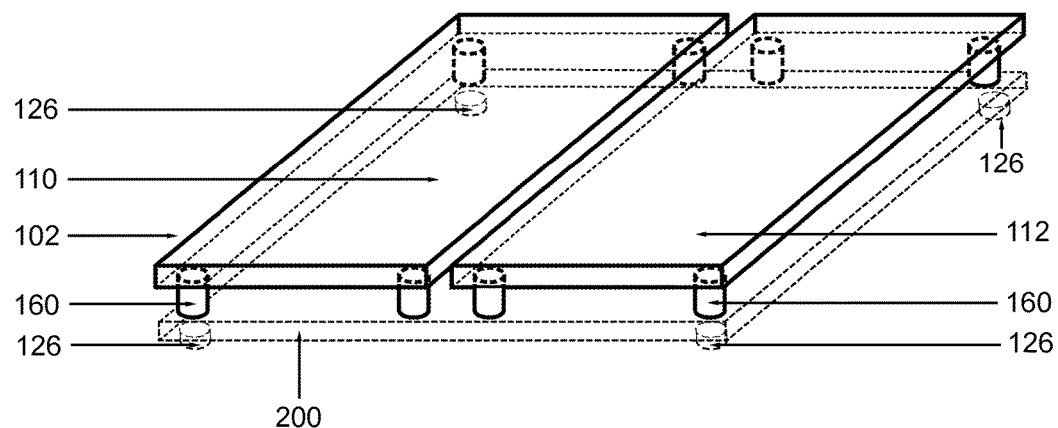
FIG. 4 is a diagrammatic perspective view of one force measurement assembly used in the systems of FIGS. 1 and 8, according to an embodiment of the invention, wherein the force measurement assembly is in the form of a dual force plate.

In the illustrated embodiment, the at least one force transducer associated with the first and second plate components 110, 112 comprises four (4) pylon-type force transducers 160 (or pylon-type load cells) that are disposed underneath, and near each of the four corners (4) of the first plate component 110 and the second plate component 112 (see FIG. 4). Each of the eight (8) illustrated pylon-type force transducers 160 has a plurality of strain gages adhered to the outer periphery of a cylindrically-shaped force transducer sensing element for detecting the mechanical strain of the force transducer sensing element imparted thereon by the force(s) applied to the surfaces of the force measurement assembly 102. As shown in FIG. 4, a base plate 200 can be provided underneath the transducers 160 of each plate component 110, 112. In some embodiments, the feet 126 are mounted on the bottom surface of this base plate 200. Also, in some embodiments, side plates are mounted between the base plate 200 and the plate components 110, 112 so as to conceal the force transducers 160.

In an alternative embodiment, rather than using four (4) pylon-type force transducers 160 on each plate component 110, 112, force transducers in the form of transducer beams could be provided under each plate component 110, 112. In this alternative embodiment, the first plate component 110 could comprise two transducer beams that are disposed underneath, and on generally opposite sides of the first plate component 110. Similarly, in this embodiment, the second plate component 112 could comprise two transducer beams that are disposed underneath, and on generally opposite sides of the second plate component 112. Similar to the pylon-type force transducers 160, the force transducer beams could have a plurality of strain gages attached to one or more surfaces thereof for sensing the mechanical strain imparted on the beam by the force(s) applied to the surfaces of the force measurement assembly 102.

Rather, than using four (4) force transducer pylons under each plate, or two spaced apart force transducer beams under each plate, it is to be understood that the force measurement assembly 102 can also utilize the force transducer technology described in U.S. Pat. No. 8,544,347, the entire disclosure of which is incorporated herein by reference.

Also, as shown in FIG. 1, the force measurement assembly 102 is provided with a plurality of support feet 126 disposed thereunder. Preferably, each of the four (4) corners of the force measurement assembly 102 is provided with a support foot 126. In some embodiment(s), each support foot 126 is attached to a bottom surface of a force transducer or a base plate. In another embodiment, one or more of the force transducers could function as support feet (e.g., if pylon-type force transducers are used, the first and second plate components 110, 112 could be supported on the force transducers). In one preferred embodiment, at least one of the support feet 126 is adjustable so as to facilitate the leveling of the force measurement assembly 102 on an uneven floor surface.

Figure 2:
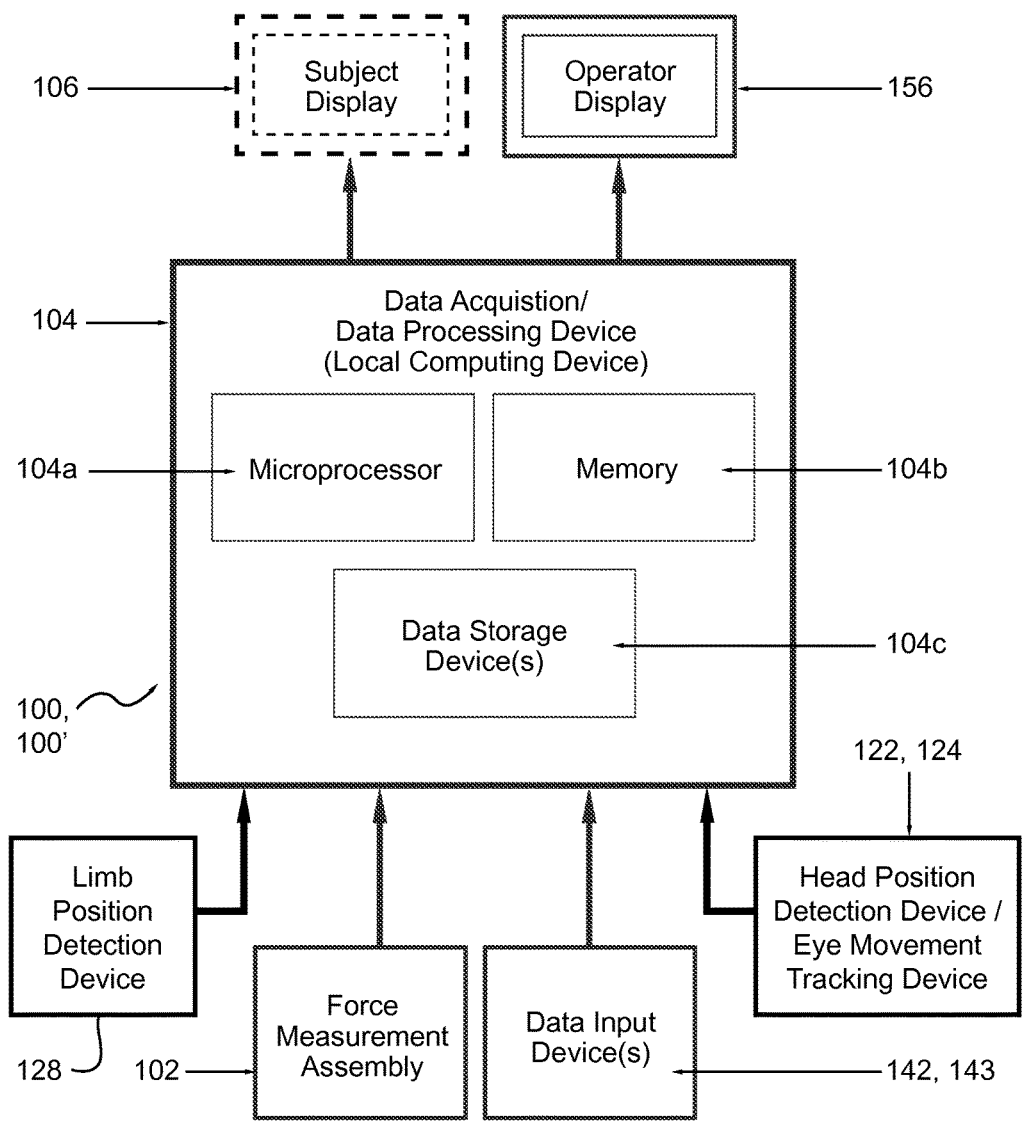
FIG. 2 is a block diagram of constituent components of the systems of FIGS. 1 and 8, according to an embodiment of the invention.

Now, turning to FIG. 2, it can be seen that the data acquisition/data processing device 104 of the system 100 of FIG. 1 comprises a microprocessor 104a for processing data, memory 104b (e.g., random access memory or RAM) for storing data during the processing thereof, and data storage device(s) 104c, such as one or more hard drives, compact disk drives, floppy disk drives, flash drives, or any combination thereof. As shown in FIG. 2, the force measurement assembly 102, the eye movement and eye position tracking device 124, and the operator visual display device 156 are operatively coupled to the data acquisition/data processing device 104 such that data is capable of being transferred between these devices 102, 104, 124, and 156. Also, as illustrated in FIG. 2, a plurality of user data input devices, such as a keyboard 142 and a mouse 143, are operatively coupled to the data acquisition/data processing device 104 so that a user is able to enter data into the data acquisition/data processing device 104. In some embodiments, the data acquisition/data processing device 104 can be in the form of a desktop computer, while in other embodiments, the data acquisition/data processing device 104 can be embodied as a laptop computer.

With reference to FIG. 1, the operator visual display device 156 of the system 100 will be described in more detail. In the illustrated embodiment, the operator visual display device 156 is in the form of a flat panel monitor. The operator visual display device 156 is operatively coupled to the data acquisition/data processing device 104 by means of data transmission cable 158. Those of ordinary skill in the art will readily appreciate that various types of flat panel monitors having various types of data transmission cables 158 may be used to operatively couple the operator visual display device 156 to the data acquisition/data processing device 104. For example, the flat panel monitor employed may utilize a video graphics array (VGA) cable, a digital visual interface (DVI or DVI-D) cable, a high-definition multimedia interface (HDMI or Mini-HDMI) cable, or a DisplayPort digital display interface cable to connect to the data acquisition/data processing device 104. Alternatively, in other embodiments of the invention, the operator visual display device 156 can be operatively coupled to the data acquisition/data processing device 104 using wireless data transmission means. Electrical power is supplied to the operator visual display device 156 using a separate power cord that connects to a building wall receptacle.

Those of ordinary skill in the art will appreciate that the operator visual display device 156 can be embodied in various forms. For example, if the operator visual display device 156 is in the form of a flat screen monitor as illustrated in FIG. 1, it may comprise a liquid crystal display (i.e., an LCD display), a light-emitting diode display (i.e., an LED display), a plasma display, a projection-type display, or a rear projection-type display. The operator visual display device 156 may also be in the form of a touch pad display.

Figure 3:
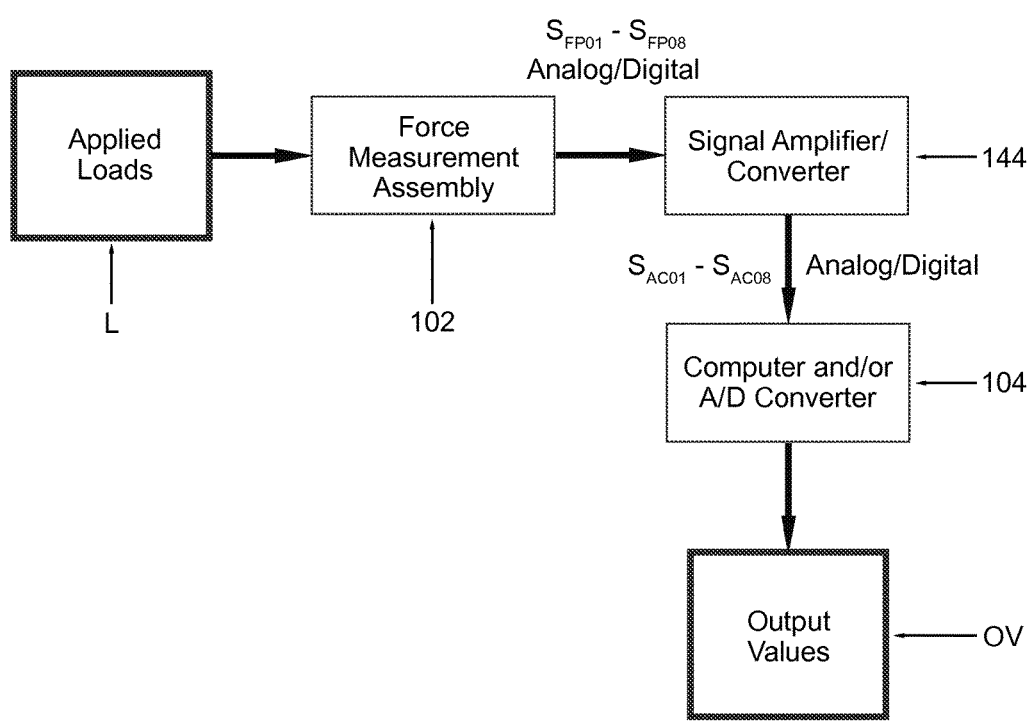
FIG. 3 is a block diagram illustrating data manipulation operations carried out by the force measurement assemblies of the systems of FIGS. 1 and 8, according to an embodiment of the invention.

FIG. 3 graphically illustrates the acquisition and processing of the load data carried out by the exemplary embodiment of the system 100 of FIG. 1. Initially, as shown in FIG. 3, a load L is applied to the force measurement assembly 102 by a subject disposed thereon. The load is transmitted from the first and second plate components 110, 112 to its respective set of pylon-type force transducers 160 or force transducer beams. As described above, in one embodiment of the invention, each plate component 110, 112 comprises four (4) pylon-type force transducers 160 disposed thereunder (e.g., see FIG. 4). Preferably, these pylon-type force transducers are disposed near respective corners of each plate component 110, 112. In a preferred embodiment of the invention, each of the pylon-type force transducers 160 includes a plurality of strain gages wired in one or more Wheatstone bridge configurations, wherein the electrical resistance of each strain gage is altered when the associated portion of the associated pylon-type force transducer undergoes deformation (i.e., a measured quantity) resulting from the load (i.e., forces and/or moments) acting on the first and second plate components 110, 112. For each plurality of strain gages disposed on the pylon-type force transducers 160, the change in the electrical resistance of the strain gages brings about a consequential change in the output voltage of the Wheatstone bridge (i.e., a quantity representative of the load being applied to the measurement surface). Thus, in one embodiment, the four (4) pylon-type force transducers 160 disposed under each plate component 110, 112 output a total of four (4) analog output voltages (signals). In another embodiment, the four (4) pylon-type force transducers 160 disposed under each plate component 110, 112 output a combined total of three (3) analog output voltages (signals). In some embodiments, the three (3) or four (4) analog output voltages from each plate component 110, 112 are then transmitted to a preamplifier board (not shown) for preconditioning. The preamplifier board is used to increase the magnitudes of the transducer analog voltages, and preferably, to convert the analog voltage signals into digital voltage signals as well. After which, the force measurement assembly 102 transmits the force plate output signals $S_{FPO1}$-$S_{FPO8}$ to a main signal amplifier/converter 144. Depending on whether the preamplifier board also includes an analog-to-digital (A/D) converter, the force plate output signals $S_{FPO1}$-$S_{FPO8}$ could be either in the form of analog signals or digital signals. The main signal amplifier/converter 144 further magnifies the force plate output signals $S_{FPO1}$-$S_{FPO8}$, and if the signals $S_{FPO1}$-$S_{FPO8}$ are of the analog-type (for a case where the preamplifier board did not include an analog-to-digital (A/D) converter), it may also convert the analog signals to digital signals. Then, the signal amplifier/converter 144 transmits either the digital or analog signals $S_{ACO1}$-$S_{ACO8}$ to the data acquisition/data processing device 104 (computer or computing device 104) so that the forces and/or moments that are being applied to the surfaces of the force measurement assembly 102 can be transformed into output values OV that can be used to determine the postural sway of the subject 108. In addition to the components 104a, 104b, 104c, the data acquisition/data processing device 104 may further comprise an analog-to-digital (A/D) converter if the signals $S_{ACO1}$-$S_{ACO8}$ are in the form of analog signals. In such a case, the analog-to-digital converter will convert the analog signals into digital signals for processing by the microprocessor 104a.

When the data acquisition/data processing device 104 receives the voltage signals $S_{ACO1}$-$S_{ACO8}$, it initially transforms the signals into output forces and/or moments by multiplying the voltage signals $S_{ACO1}$-$S_{ACO8}$ by a calibration matrix. After which, the force $F_L$ exerted on the surface of the first force plate by the left foot of the subject, the force $F_R$ exerted on the surface of the second force plate by the right foot of the subject, and the center of pressure for each foot of the subject (i.e., the x and y coordinates of the point of application of the force applied to the measurement surface by each foot) are determined by the data acquisition/data processing device 104. The computations performed in the determination of the forces and center of pressure are described hereinafter.

While, in one exemplary embodiment described hereinafter, the data acquisition/data processing device 104 determines the vertical forces $F_{Lz}$, $F_{Rz}$ exerted on the surface of the first and second force plates by the feet of the subject and the center of pressure for each foot of the subject, it is to be understood that the invention is not so limited. Rather, in other embodiments of the invention, the output forces of the data acquisition/data processing device 104 could include all three (3) orthogonal components of the resultant forces acting on the two plate components 110, 112. In yet other embodiments of the invention, the output forces and moments of the data acquisition/data processing device 104 can be in the form of other forces and moments as well.

Referring again to FIG. 1, it can be seen that the subject 108 is also provided with the eye movement and eye position tracking device 124 that is configured to track the eye movement and eye position of the subject 108 while he performs a balance test and/or a concussion screening test. In the illustrated embodiment, the eye movement and eye position tracking device 124 is used in conjunction with the postural sway detection device (i.e., force plate 102). The eye movement and eye position tracking device 124 may incorporate one or more video cameras for capturing an image of one of the subject's eye or images of both of the subject's eyes (i.e., one camera dedicated to each one of the subject's eyes). In one or more embodiments, the video cameras of the eye movement and eye position tracking device 124 may comprise infrared cameras in order to enable accurate images of the eye to be captured even in low light environments. The one or more video cameras of the eye movement and eye position tracking device 124 may capture at least sixty (60) frames per second. In one or more embodiments, only approximately a quarter of the pixels in each image captured by the one or more cameras may be downloaded (i.e., the part of the image centered around the eye) in order to increase the minimum resolution of the camera to 250 frames per second (i.e., 250 Hz) by decreasing the image size being downloaded by approximately one-quarter. In an alternative embodiment, the eye movement and eye position tracking device 124 may be in the form of the eye movement tracking devices described in U.S. Pat. Nos. 6,113,237 and 6,152,564, the entire disclosures of which are incorporated herein by reference. The eye movement and eye position tracking device 124 is configured to output one or more signals that are representative of the detected eye movement and position of the subject 108 (e.g., the slow and fast eye movements of the subject). As explained above, the eye movement and eye position tracking device 124 may be operatively connected to the data acquisition/data processing device 104 for data collection and analysis of the eye movement and position data acquired by the eye movement and eye position tracking device 124 (e.g., by using wireless data transmission means). As such, using the output signals from the eye movement and eye position tracking device 124, the data acquisition/data processing device 104 may be specially programmed to determine the eye movement and position of the subject 108 during the performance of the balance test and/or the concussion screening test.

Now, the functionality of the system 100 for measuring postural sway, eye movement and/or eye position, and gaze direction will be described in detail. It is to be understood that the aforedescribed functionality of the system 100 of FIG. 1 can be carried out by the data acquisition/data processing device 104 utilizing software, hardware, or a combination of both hardware and software. For example, the data acquisition/data processing device 104 can be specially programmed to carry out the functionality described hereinafter. In one embodiment of the invention, the computer program instructions necessary to carry out this functionality may be loaded directly onto an internal data storage device 104c of the data acquisition/data processing device 104 (e.g., on a hard drive thereof) and subsequently executed by the microprocessor 104a of the data acquisition/data processing device 104. Alternatively, these computer program instructions could be stored on a portable computer-readable medium (e.g., a flash drive, a floppy disk, a compact disk, etc.), and then subsequently loaded onto the data acquisition/data processing device 104 such that the instructions can be executed thereby. In other embodiments, these computer program instructions could be embodied in the hardware of the data acquisition/data processing device 104, rather than in the software thereof. It is also possible for the computer program instructions to be embodied in a combination of both the hardware and the software.

Figure 5:
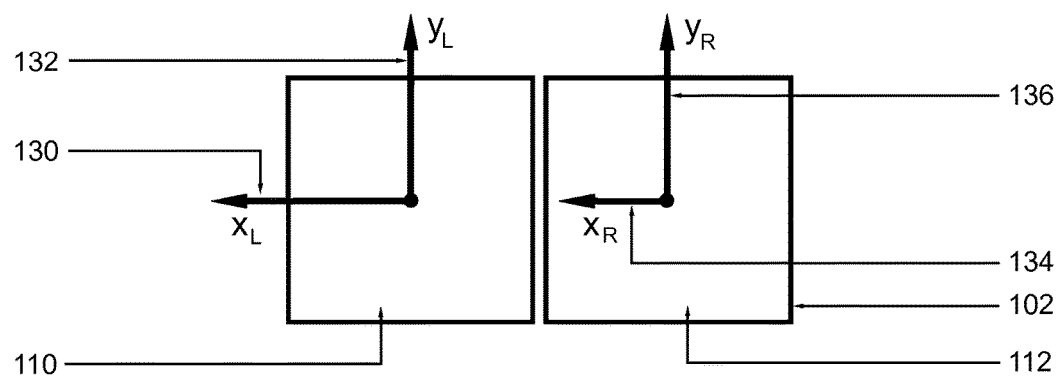
FIG. 5 is a diagrammatic top view of one force measurement assembly used in the systems of FIGS. 1 and 8 with exemplary coordinate axes superimposed thereon, according to an embodiment of the invention, wherein the force measurement assembly is in the form of a dual force plate.

In the illustrated embodiment, the data acquisition/data processing device 104 is configured to compute the postural sway of the subject 108. As described above, when the data acquisition/data processing device 104 receives the voltage signals $S_{ACO1}$-$S_{ACO6}$, it initially transforms the signals into output forces and/or moments by multiplying the voltage signals $S_{ACO1}$-$S_{ACO6}$ by a calibration matrix (e.g., $F_{Lz}$, $M_{Lx}$, $M_{Ly}$, $F_{Rz}$, $M_{Rx}$, $M_{Ry}$). After which, the center of pressure for each foot of the subject (i.e., the x and y coordinates of the point of application of the force applied to the measurement surface by each foot) are determined by the data acquisition/data processing device 104. Referring to FIG. 5, which depicts a top view of the measurement assembly 102, it can be seen that the center of pressure coordinates ($x_{P_L}$, $y_{P_L}$) for the first plate component 110 are determined in accordance with x and y coordinate axes 130, 132. Similarly, the center of pressure coordinates ($x_{P_R}$, $y_{P_R}$) for the second plate component 112 are determined in accordance with x and y coordinate axes 134, 136. If the force transducer technology described in U.S. Pat. No. 8,544,347 is employed, it is to be understood that the center of pressure coordinates ($x_{P_L}$, $y_{P_L}$, $x_{P_R}$, $x_{P_R}$) can be computed in the particular manner described in that patent.

Figure 6:
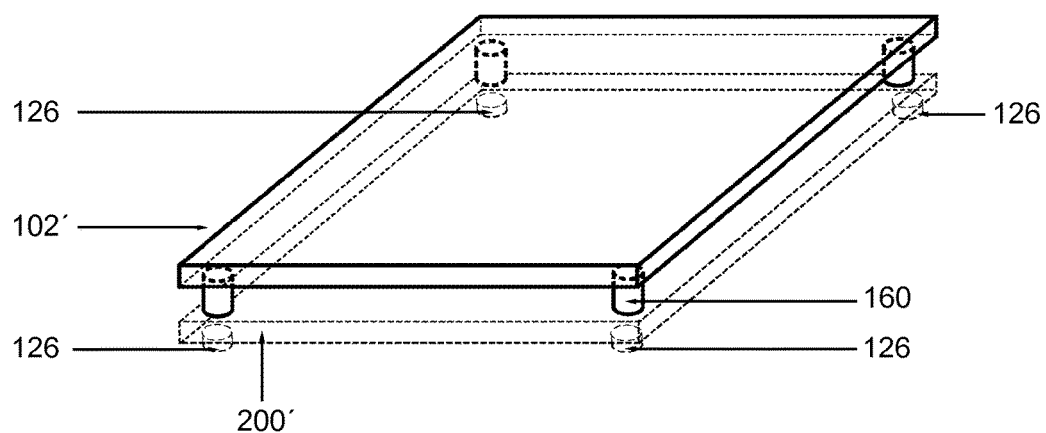
FIG. 6 is a diagrammatic perspective view of another force measurement assembly used in the systems of FIGS. 1 and 8, according to an embodiment of the invention, wherein the force measurement assembly is in the form of a single force plate.
Figure 7:
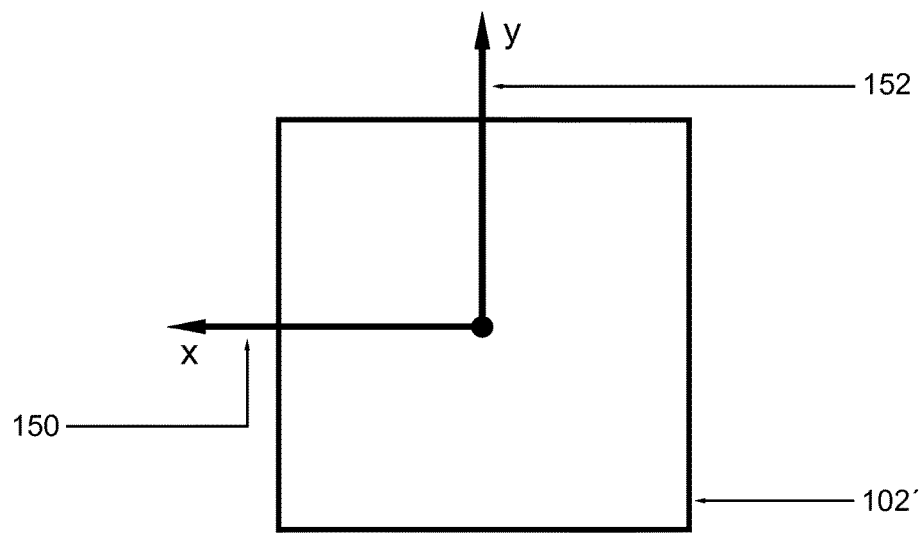
FIG. 7 is a diagrammatic top view of another force measurement assembly used in the systems of FIGS. 1 and 8 with exemplary coordinate axes superimposed thereon, according to an embodiment of the invention, wherein the force measurement assembly is in the form of a single force plate.

As explained above, rather than using a force measurement assembly 102 having first and second plate components 110, 112, a force measurement assembly 102' in the form of a single force plate may be employed (see FIGS. 6 and 7, which illustrate a single force plate). Similar to that described above for the dual force plate of FIG. 4, a base plate 200' can be provided underneath the transducers 160 of the single force plate illustrated in FIG. 6. Unlike the dual force plate assembly illustrated in FIG. 4, the single force plate comprises a single measurement surface on which both of a subject's feet are placed during testing. As such, rather than computing two sets of center of pressure coordinates (i.e., one for each foot of the subject), the embodiments employing the single force plate compute a single set of overall center of pressure coordinates ($x_P$, $y_P$) in accordance with x and y coordinate axes 150, 152. The manner in which the center of pressure coordinates are computed for the single force plate assembly is the same as that described above for a single plate of the dual force plate assembly, except that there will only be a single set of center of pressure coordinates (e.g., coordinates $x_P$, $y_P$) for a single measurement surface, rather than two sets of coordinates ($x_{P_L}$, $y_{P_L}$; $x_{P_R}$, $y_{P_R}$) described above for the two independent measurement surfaces 114, 116 of the dual force plate assembly.

In one exemplary embodiment, the data acquisition/data processing device 104 determines the vertical forces $F_{Lz}$, $F_{Rz}$ exerted on the surface of the first and second force plates by the feet of the subject and the center of pressure for each foot of the subject, while in another exemplary embodiment, the output forces of the data acquisition/data processing device 104 include all three (3) orthogonal components of the resultant forces acting on the two plate components 110, 112 (i.e., $F_{Lx}$, $F_{Ly}$, $F_{Lz}$, $F_{Rx}$, $F_{Ry}$, $F_{Rz}$) and all three (3) orthogonal components of the moments acting on the two plate components 110, 112 (i.e., $M_D$, $M_{Ly}$, $M_{Lz}$, $M_{Rx}$, $M_{Ry}$, $M_{Rz}$). In yet other embodiments of the invention, the output forces and moments of the data acquisition/data processing device 104 can be in the form of other forces and moments as well.

In the exemplary embodiments where only the vertical forces $F_{Lz}$, $F_{Rz}$ are determined, the one or more numerical values determined from the output signals of the force transducers associated with the first plate component 110 may include x and y coordinates (e.g., coordinates $x_{P_L}$, $y_{P_L}$) specifying the center of pressure of a first force vector (e.g., left force vector $\vec{F}_L$) applied by the subject to the first measurement surface 114 of the first plate component 110 (e.g., left plate) by the subject. Similarly, the one or more numerical values determined from the output signals of the force transducers associated with the second plate component 112 further include x and y coordinates (e.g., coordinates $x_{P_R}$, $y_{P_R}$) specifying the center of pressure of a second force vector (e.g., right force vector $\vec{F}_R$) applied by the subject to the second measurement surface 116 of the second plate component 112 (e.g., right plate) by the subject. If the left and right force plates of the force measurement assembly 102 are configured as 3-component force measurement devices (i.e., the transducers of these plates are capable of collectively measuring $F_z$, $M_x$, $M_y$), then the center of pressure of the first force vector $\vec{F}_L$ applied by the subject to the first measurement surface 114 of the first plate component 110 is computed as follows:

$$x_{P_L} = \frac{-M_{y_L}}{F_{z_L}} \quad (1)$$

$$y_{P_L} = \frac{M_{x_L}}{F_{z_L}} \quad (2)$$

where:
$x_{P_L}$, $y_{P_L}$: coordinates of the point of application for the force (i.e., center of pressure) on the first plate component 110 (left force plate);
$F_{z_L}$: z-component of the resultant force acting on the first plate component 110 (left force plate);
$M_{x_L}$: x-component of the resultant moment acting on the first plate component 110 (left force plate); and
$M_{y_L}$: y-component of the resultant moment acting on the first plate component 110 (left force plate).

Similarly, when the left and right force plates of the force measurement assembly 102 are configured as 3-component force measurement devices, the center of pressure of the second force vector $\vec{F}_R$ applied by the subject to the second measurement surface 116 of the second plate component 112 is computed as follows:

$$x_{P_R} = \frac{-M_{y_R}}{F_{z_R}} \quad (3)$$

$$y_{P_R} = \frac{M_{x_R}}{F_{z_R}} \quad (4)$$

$x_{P_R}$, $y_{P_R}$: coordinates of the point of application for the force (i.e., center of pressure) on the second plate component 112 (right force plate);
$F_{z_R}$: z-component of the resultant force acting on the second plate component 112 (right force plate);
$M_{x_R}$: x-component of the resultant moment acting on the second plate component 112 (right force plate); and
$M_{y_R}$: y-component of the resultant moment acting on the second plate component 112 (right force plate).

However, if the left and right force plates of the force measurement assembly 102 are configured as 6-component force measurement devices (i.e., the transducers of these plates are capable of collectively measuring $F_x$, $F_y$, $F_z$, $M_x$, $M_y$, $M_z$), then the center of pressure of the first force vector $\vec{F}_L$ applied by the subject to the first measurement surface 114 of the first plate component 110 is computed as follows:

$$x_{P_L} = \frac{-h_L \cdot F_{x_L} - M_{y_L}}{F_{z_L}} \quad (5)$$

$$y_{P_L} = \frac{-h_L \cdot F_{y_L} + M_{x_L}}{F_{z_L}} \quad (6)$$

where:
$h_L$: thickness above the top surface of any material covering the first plate component 110 (left force plate);
$F_{x_L}$: x-component of the resultant force acting on the first plate component 110 (left force plate); and
$F_{y_L}$: y-component of the resultant force acting on the first plate component 110 (left force plate).

Similarly, when the left and right force plates of the force measurement assembly 102 are configured as 6-component force measurement devices, the center of pressure of the second force vector $\vec{F}_R$ applied by the subject to the second measurement surface 116 of the second plate component 112 is computed as follows:

$$x_{P_R} = \frac{-h_R \cdot F_{x_R} - M_{y_R}}{F_{z_R}} \quad (7)$$

$$y_{P_R} = \frac{-h_R \cdot R_{y_R} + M_{x_R}}{F_{z_R}} \quad (8)$$

where:

$h_R$: thickness above the top surface of any material covering the second plate component 112 (right force plate);

$F_{x_R}$: x-component of the resultant force acting on the second plate component 112 (right force plate); and $F_{y_R}$: y-component of the resultant force acting on the second plate component 112 (right force plate).

In an exemplary embodiment where only the single force plate of FIGS. 6 and 7 is utilized, and only the vertical force $F_z$ is determined, the one or more numerical values determined from the output signals of the force transducers associated with the force plate 102' may include x and y coordinates (e.g., coordinates $x_P$, $y_P$) specifying the center of pressure of a force vector (e.g., a force vector $\vec{F}$) applied by the subject to the single measurement surface of the single force plate 102'. Also, if the force plate 102' is configured as a 3-component force measurement device (i.e., the transducers of this plate are capable of collectively measuring $F_z$, $M_x$, $M_y$), then the center of pressure of the force vector $\vec{F}$ applied by the subject to the measurement surface of the force plate 102' is computed as follows:

$$x_P = \frac{-M_y}{F_Z} \qquad (9)$$

$$y_P = \frac{M_x}{F_Z} \qquad (10)$$

where:

$x_P$, $y_P$: coordinates of the point of application for the force (i.e., center of pressure) on the single force plate 102';

$F_Z$: z-component of the resultant force acting on the single force plate 102';

$M_x$: x-component of the resultant moment acting on the single force plate 102'; and $M_y$: y-component of the resultant moment acting on the single force plate 102'.

In one or more embodiments, the data acquisition/data processing device 104 may convert the computed center of pressure (COP) to a center of gravity (COG) for the subject using a Butterworth filter. For example, in one exemplary, non-limiting embodiment, a second-order Butterworth filter with a 0.75 Hz cutoff frequency is used. In addition, the data acquisition/data processing device 104 also computes a sway angle for the subject using a corrected center of gravity (COG') value, wherein the center of gravity (COG) value is corrected to accommodate for the offset position of the subject relative to the origin of the coordinate axes (130, 132, 134, 136) of the force plate assembly 102 or the offset position of the subject relative to the origin of the coordinate axes (150, 152) of the force plate assembly 102'. For example, the data acquisition/data processing device 104 computes the sway angle for the subject in the following manner:

$$\theta = \sin^{-1}\left(\frac{COG'}{0.55h}\right) - 2.3° \qquad (11)$$

where:

$\theta$: sway angle of the subject;

COG': corrected center of gravity of the subject; and h: height of the center of gravity of the subject.

Figure 10:
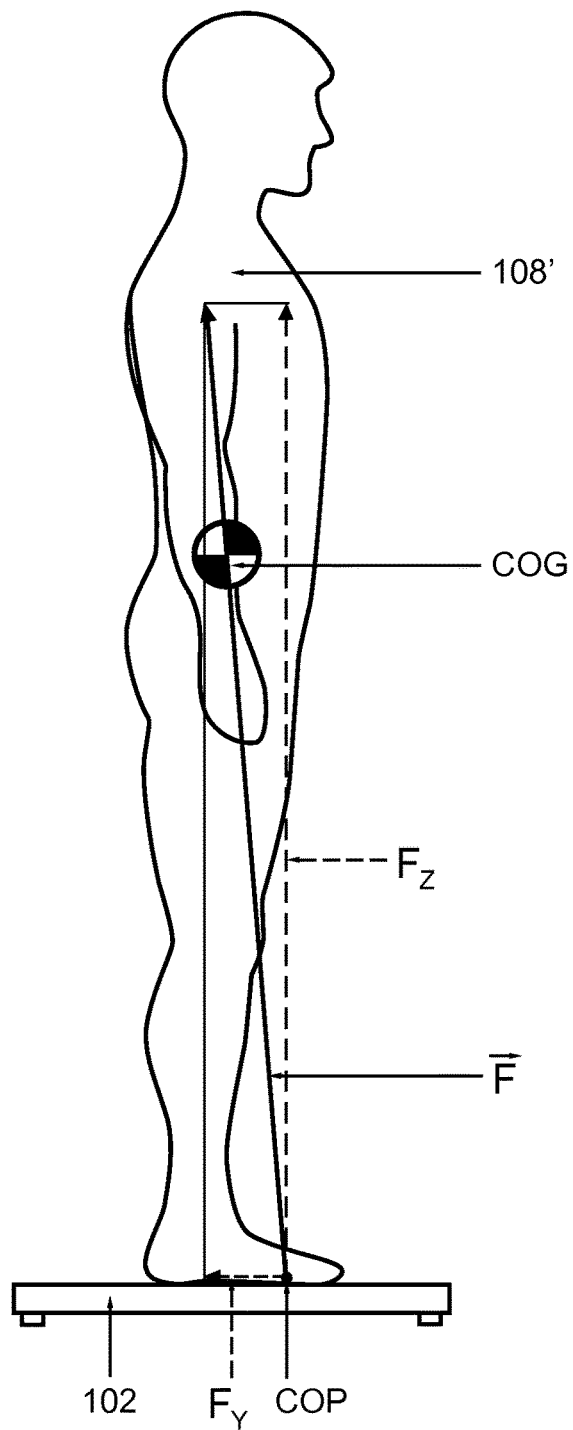
FIG. 10 is a diagrammatic side view of a subject disposed on a surface of a force plate, wherein the center of pressure (COP) and the center of gravity (COG) of the subject are depicted thereon along with the vertical force and shear force components.

In one or more other alternative embodiments, the data acquisition/data processing device 104 may directly calculate the center of gravity for the subject. Initially, referring to FIG. 10, a side view of a subject 108' disposed on a surface of a force plate 102 is diagrammatically illustrated. As shown in this figure, the ground reaction force vector $\vec{F}$ passes through the center of pressure (COP) for the subject and the subject's center of gravity (COG). For the purpose of the analysis, the ground reaction force vector $\vec{F}$ can be represented by its constituent components, namely its vertical force component $F_Z$ and its shear force component $F_Y$. It is to be noted that, for the purposes of this analysis, only the sagittal plane of the subject is being considered.

Figure 11:
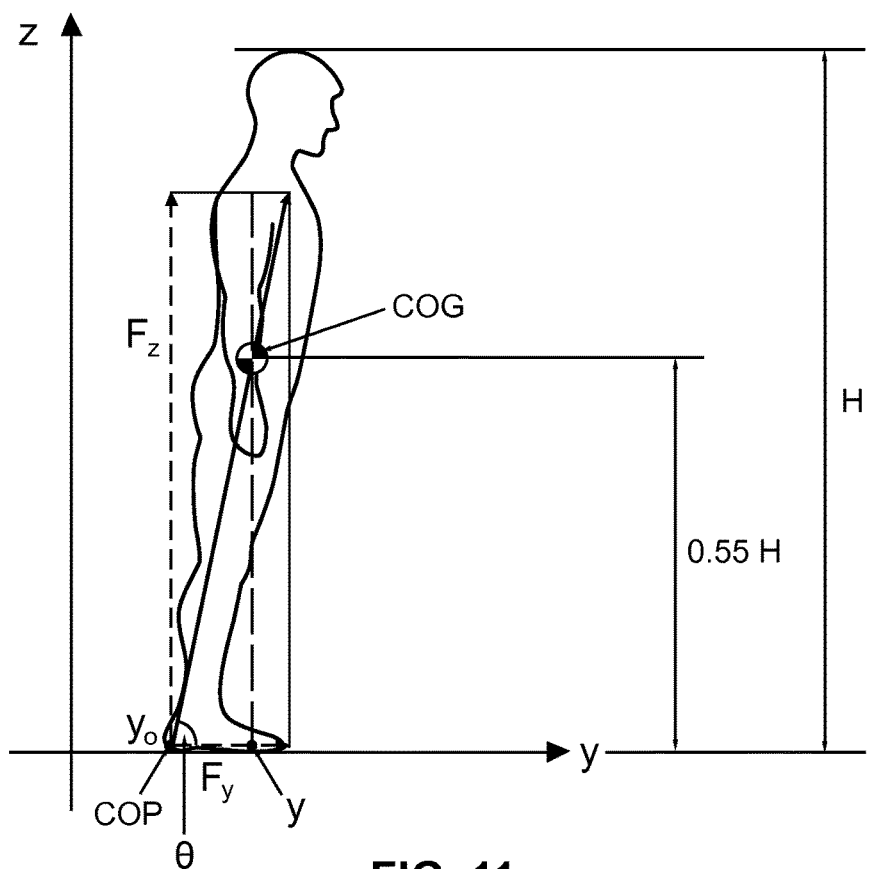
FIG. 11 is a free body diagram of a subject illustrating the force components and parameters that are used in computing center of gravity (COG) of the subject.

Then, with reference to FIG. 11, it can be seen that the y-coordinate (y) of the subject's center-of-gravity is the unknown parameter being computed by the data acquisition/data processing device 104. The center of pressure (COP) y-coordinate ($y_0$) is known from the force plate output (e.g., refer to the calculations described above). Also, as shown in FIG. 11, the following trigonometric relationship exists between the angle $\theta$, the vertical force component $F_Z$, and the shear force component $F_Y$:

$$\tan\theta = \frac{F_Z}{F_Y} \qquad (12)$$

Figure 12:
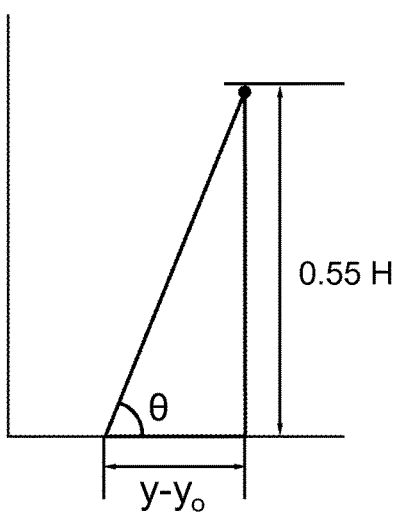
FIG. 12 is a trigonometric diagram that is used in computing center of gravity (COG) of the subject.

Now, turning to FIG. 12, it can be seen that the tangent of the angle $\theta$ is also equal to the following:

$$\tan\theta = \frac{0.55H}{y - y_0} \qquad (13)$$

where:

H: height of the subject;

y: y-coordinate of the center of gravity (COG) of the subject; and $y_0$: y-coordinate of the center of pressure (COP) of the subject determined from the force plate output.

Thus, it follows that equations (12) and (13) can be combined to obtain the following relationship:

$$\frac{0.55H}{y - y_0} = \frac{F_Z}{F_Y} \qquad (14)$$

This equation (14) can be initially rearranged as follows:

$$y - y_0 = \frac{F_Y}{F_Z}(0.55H) \qquad (15)$$

Finally, to solve for the unknown y-coordinate (y) of the subject's center of gravity, equation (15) is rearranged in the following manner:

$$y = y_0 + \frac{F_Y}{F_Z}(0.55H) \qquad (16)$$

Therefore, the y-coordinate (y) of the subject's center of gravity can then be determined as a function of the y-coordinate ($y_0$) of the subject's center of pressure, the shear force component $F_Y$, the vertical force component $F_Z$, and the height of the subject H. The y-coordinate ($y_0$) of the subject's center of pressure, the shear force component $F_Y$, and the vertical force component $F_Z$ are all determined from the output of the force plate, whereas the height of the subject can be entered into the data acquisition/data processing device 104 by the user of the system (i.e., after the system user acquires the height value from the subject being tested). Advantageously, the computational method described above enables the subject's center of gravity to be accurately determined using the force measurement system.

In one or more embodiments, a method for concurrently measuring the eye movement and/or eye position and postural sway of a subject is performed using the system illustrated in FIG. 1. Initially, the subject 108 is positioned in an upright position on a surface or surfaces (e.g., the first and second measurement surfaces 114, 116 of the dual force plate 102 in FIG. 1). Then, the eye movement and eye position of the subject 108 is measured using the eye movement tracking device 124. The eye movement tracking device 124 outputs one or more first signals that are representative of the detected eye movement and eye position of the subject 108 to the data acquisition/data processing device 104. In addition, the postural sway of the subject 108 is measured using a postural sway detection device (i.e., the force plate 102 in FIG. 1) while the eye movement and eye position of the subject 108 is simultaneously measured by the eye movement tracking device 124. The postural sway detection device (i.e., force plate 102) outputs the one or more second signals that are representative of the postural sway of the subject to the data acquisition/data processing device 104. After which, the data acquisition/data processing device 104 is specially programmed to determine the eye movement and eye position data for the subject 108 from the one or more first signals output by the eye movement tracking device 124. The data acquisition/data processing device 104 also is specially programmed to determine postural sway data for the subject 108 from the one or more second signals output by the postural sway detection device (i.e., force plate 102).

Figure 13:
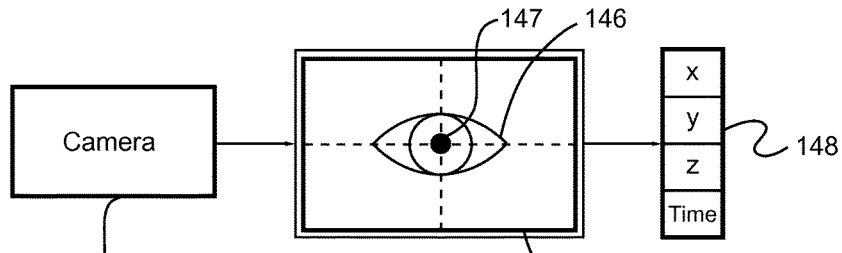
FIG. 13 is diagrammatic representation of the output generated by an eye movement tracking device.

Next, an illustrative manner in which the data acquisition/data processing device 104 of the system 100 in FIG. 1 performs the eye movement and eye position calculations will be explained in detail. Referring to FIG. 13, it can be seen that the eye movement tracking device 124 comprises one or more cameras 138 (e.g., two cameras, one for each eye of the subject) Each of the one or more cameras 138 captures a time-stamped image 140 of a respective eye 146 of the subject 108. For example, in one or more embodiments, the location of the pupil 147 of the eye 146 may be extracted from a grayscale image 140. Because the pupil is darker than the remainder of the image (i.e., the pupil is generally black in a grayscale image), its location is easily extracted from the camera image 140. The location of the pupil 147 of the eye 146 is defined in terms of pupil coordinates within the image 140 (i.e., the pupil coordinates may correspond to the pixel coordinates of the image). As shown in FIG. 13, using the information from the time-stamped image 140, the data acquisition/data processing device 104 may generate output data 148 that includes the x, y, and z coordinates of the center point of the pupil 147 of the eye 146 and the time at which the image 140 was taken. The x and y coordinates of the center point of the pupil 147 represent its horizontal and vertical positions in the image 140, respectively, while the z coordinate is the torsional coordinate that represents the angular position of the subject's eyeball in the eye socket of the subject 108.

Figure 14:
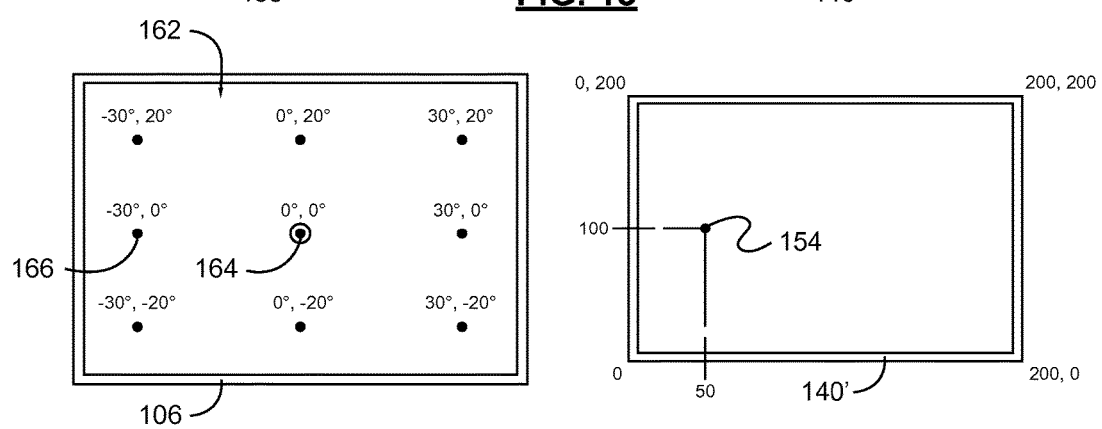
FIG. 14 is diagrammatic representation of a calibration procedure carried out in conjunction with the eye movement tracking device.

With reference to FIG. 14, an illustrative calibration procedure for correlating the eye position of the subject 108 within the eye image 140' with an angular position of the eye will be described. In FIG. 14, a subject visual display device 106 is depicted on the left side of this figure, while an eye image 140' is depicted on the right side of this figure. For the sake of clarity, the image of the actual eye has been excluded from the eye image 140', and the position of the pupil of the subject's eye is represented by a single point 154. As shown on the left side of FIG. 14, the subject visual display device 106 comprises a screen image 162 with a plurality of points arranged in a grid pattern. In the screen image 162, the center point 164 corresponds to a zero angular position in both the horizontal and vertical directions (i.e., 0°,0°). The top row of points in the screen image 162 each have a vertical angular position of 20 degrees, the middle row of points each have a vertical angular position of 0 degrees, and the bottom row of points each have a vertical angular position of −20 degrees. The leftmost column of points in the screen image 162 each have a horizontal angular position of −30 degrees, the middle column of points each have a horizontal angular position of 0 degrees, and the rightmost column of points each have a horizontal angular position of 30 degrees. Initially, during the calibration procedure, the subject 108 may be instructed to focus on the center point 164 (i.e., the 0°, 0° point) in the screen image 162, which is correlated with the center position of the subject's eye in the eye image 140' (i.e., with pixel coordinates 100, 100). Then, during the calibration procedure, the subject 108 may be instructed to focus on the point 166 (i.e., the −30°, 0° point) in the screen image 162, which is correlated with the point 154 in the eye image 140' (i.e., with pixel coordinates 50, 100) representing the center point of the pupil of the subject's eye. In this manner, as the subject 108 is instructed to focus on each of the nine points in the screen image 162 of FIG. 14, the coordinates representing the center point of the pupil of the subject's eye are correlated with the angular position of the subject's eye in both the horizontal and vertical directions. As such, during the tests described hereinafter, once the coordinate of the subject's eye is determined, the angular position of the subject's eye may be easily determined using the results of the calibration procedure described above.

After the data acquisition/data processing device 104 determines the eye movement and eye position data and the postural sway data for the subject 108, the data acquisition/data processing device 104 may be specially programmed to further determine a first numerical score for the subject 108 based upon the eye movement and eye position data, and a second numerical score for the subject 108 based upon the postural sway data. Then, the data acquisition/data processing device 104 may be specially programmed to combine the first numerical score with the second numerical score to obtain an overall combined sway and eye movement score for the subject.

Similarly, after the data acquisition/data processing device 104 determines the eye movement and eye position data and the postural sway data for the subject 108, the data acquisition/data processing device 104 may be specially programmed to determine one or more eye movement deviation values based upon the eye movement and eye position data determined for the subject 108. The one or more eye movement deviation values quantify instances during the balance test and/or the concussion screening test where the subject is unable to follow a particular target. The data acquisition/data processing device 104 may be specially programmed to further determine a balance sway score for the subject 108 based upon the postural sway data determined for the subject 108, and then compute an adjusted balance sway score for the subject 108 by increasing the balance sway score determined for the subject 108 by a numerical factor proportionate to the one or more eye movement deviation values.

For example, in an illustrative embodiment, a balance sway score of the subject 108 may comprise one of the following: (i) a maximum sway of center-of-pressure (COP) (e.g., plus or minus 15 millimeters), (ii) a maximum sway of center-of-gravity (COG) about the ankle (e.g., plus or minus 7 degrees), and (iii) an area of ellipse fitted around the path of the COP with, for example, a 90 percent confidence area (e.g., 4.0 sq. centimeters). In the illustrative embodiment, the eye score of the subject 108 may comprise a measurement of how far behind the eyes lag the target (e.g., 10 degrees). Considering the above examples, an illustrative combined sway and eye movement score of the subject 108 may comprise one of the following: (i) a balance sway score of 15 millimeters multiplied by the eye score of 10 degrees so as to obtain a combined sway and eye movement score of 150 (i.e., 15×10), (ii) a balance sway score of 7 degrees multiplied by the eye score of 10 degrees so as to obtain a combined sway and eye movement score of 70 (i.e., 7×10), and (iii) a balance sway score of 4.0 sq. centimeters multiplied by the eye score of 10 degrees so as to obtain a combined sway and eye movement score of 40 (i.e., 4×10), depending on which of the above balance scoring techniques is utilized. The final score result(s) may be compared with the score for a normal subject. When one or more of the individual scores or their product (as illustrated above) is not normal, this may be indicative of a possible concussion.

In an alternative illustrative embodiment, the eye movements of the subject 108 may be defined by the ratio of peak eye velocity to peak target velocity (i.e., gain). For example, when the subject 108 is able to track the target perfectly, the gain will be close to 1.0 (e.g., between 0.9 and 1.0). Conversely, when the subject is unable to track the target, the gain will be closer to zero (e.g., between 0.1 and 0.2). In addition, in this illustrative embodiment, fast eye movements may be characterized based on their accuracy, velocity, and latency (i.e., the time required to initiate eye movements). For example, the numbers for a normal subject are: 90% accuracy, 400 deg/sec velocity, and 200 millisecond latency. All of these values may be summarized in a single number (i.e., a hybrid value) to quantify the eye movements. In this illustrative embodiment, when the raw gain is used as the eye score for the subject 108, the eye score decreases with increased abnormality. Although, in order for the eye score to increase with increased abnormality, the inverse of the gain may be used in lieu of the raw gain (e.g., 1/0.1 produces a larger eye score than 1/0.9). Also, when the inverse of the gain is used for the eye score, the product of an abnormal balance sway score and an abnormal eye score results in a larger combined sway and eye movement score, as described in the illustrative embodiment described above. As such, subjects or patients who are concussed would have a higher combined sway and eye movement score than subjects or patients who are not concussed.

Figure 15:
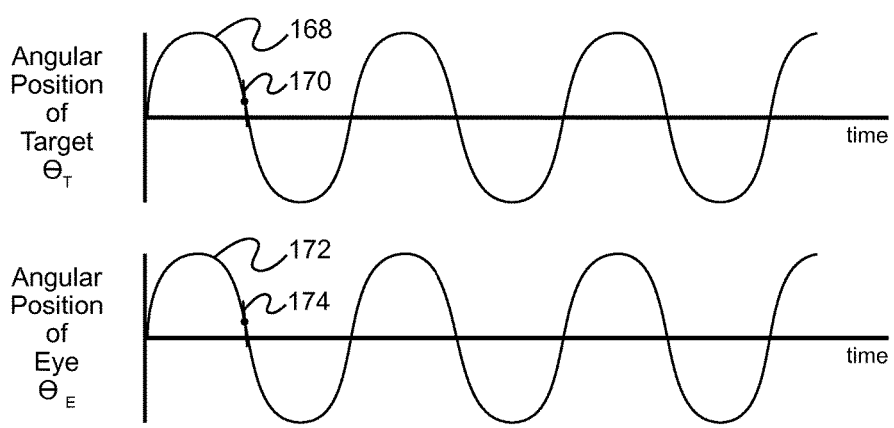
FIG. 15 illustrates exemplary graphs of angular position for a target and the associated angular position of an eye following the target.

With reference to FIG. 15, an exemplary manner for determining the gain for eye movements of the subject 108 will be described. In FIG. 15, the top sinusoidal curve 168 represents angular position of the target ($\theta_T$) over time, whereas the bottom sinusoidal curve 172 represents angular position of the subject's eye ($\theta_E$) over time. The gain for a subject 108 is computed by determining the peak target velocity from the peak slope 170 of the curve 168 (i.e. computing the derivative of the curve 168 at its peak slope location), and by determining the peak eye velocity from the peak slope 174 of the curve 172 (i.e. computing the derivative of the curve 172 at its peak slope location). Then, the gain value is determined by computing the ratio of the peak eye velocity to the peak target velocity.

Figure 16:
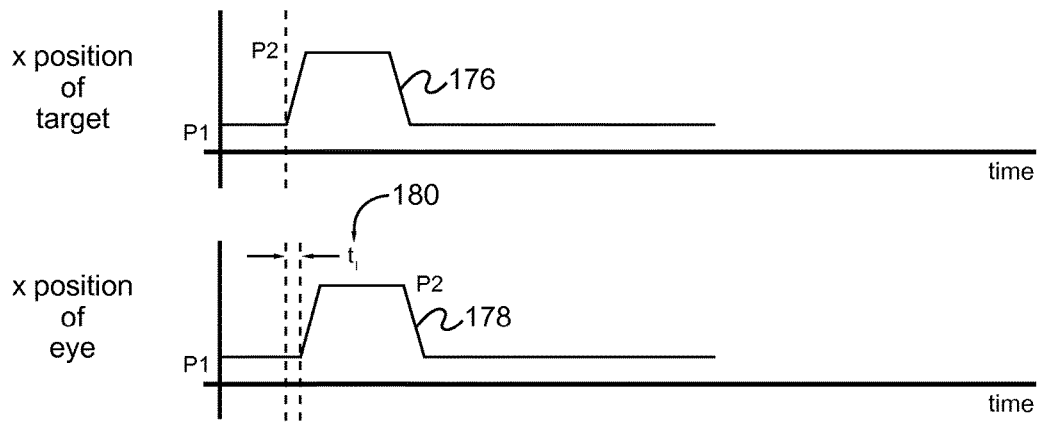
FIG. 16 illustrates exemplary graphs of horizontal position for a target and the associated horizontal position of an eye following the target, wherein the graphs illustrate a time lag between the horizontal eye position and the horizontal target position.

Next, referring to FIG. 16, an exemplary manner for determining the latency or time lag for eye movements of the subject 108 will be described. In FIG. 16, the top curve or function 176 represents the horizontal position of the target over time (i.e., the x coordinate position of the target over time), whereas the bottom curve or function 178 represents the horizontal position of the subject's eye over time (i.e., the x coordinate position of the subject's eye over time). As shown in FIG. 16, the target and the subject's eye generally move between a first position (P1) and a second position (P2). During the eye test that generates the curves 176, 178, the subject 108 is instructed to follow the target with his or her eyes as closely as possible. In FIG. 16, it can be seen that the subject's eye lags behind the target in moving from the first position (P1) to the second position (P2) by a time lag amount ($t_1$) 180. In other words, it takes the subject's eye a certain amount of time ($t_1$) to start moving after the target has already starting moving (i.e., the subject's eye is unable to react instantaneously to the movement of the target). The subject's time lag 180 is computed by comparing the target position curve 176 to the eye position curve 178.

Figure 17:
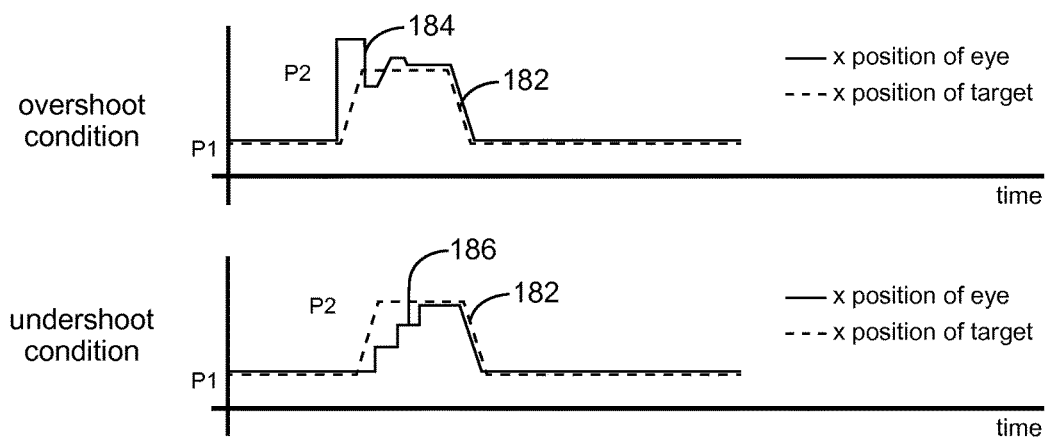
FIG. 17 illustrates exemplary graphs depicting accuracy associated with an eye following a target, wherein both an overshoot condition and an undershoot condition are shown.

Turning to FIG. 17, an exemplary manner for determining the accuracy of eye movements by the subject 108 will be explained. In the graphs of FIG. 17, the dashed line curve or function 182 represents the horizontal position of the target over time (i.e., the x coordinate position of the target over time), whereas the solid line curves or functions 184, 186 represent the horizontal position of the subject's eye over time (i.e., the x coordinate position of the subject's eye over time). As shown in FIG. 17, the target and the subject's eye generally move between a first position (P1) and a second position (P2). During the eye test that generates the curves 182, 184, 186, the subject 108 is instructed to track the target with his or her eyes as closely as possible. The top graph of FIG. 17 illustrates an overshoot condition where the subject initially overshoots the second position (P2) of the target with his or her eyes (e.g., the subject overshoots the target by 120%). Conversely, the bottom graph of FIG. 17 illustrates an undershoot condition where the subject initially undershoots the second position (P2) of the target with his or her eyes (e.g., the subject undershoots the target by 50%).

While the eye movement and/or eye position of the subject is being determined in conjunction with the postural sway of the subject in the testing procedure described above, the subject may be instructed to perform a variety of different vestibular or ocular motor tests. In particular, the subject may be instructed to perform any one or more of the following vestibular or ocular motor tests: (i) a test involving smooth pursuits, (ii) a test involving saccades, (iii) a near point convergence (NPC) test, (iv) a vestibular-ocular reflex (VOR) test, and (v) a visual motion sensitivity (VMS) test. Each of these various vestibular or ocular motor tests will be explained below.

A smooth pursuits test evaluates the ability of a subject's eye to follow a slowly moving target. During this test, the subject and the clinician may be seated, or the clinician may be standing while the subject is also standing. During this test, the clinician holds an object (e.g., his or her fingertip) a predetermined distance from the subject (e.g., a distance between two and four feet). The subject is instructed by the clinician to maintain focus on the object as the clinician horizontally displaces the object in a smooth manner a predetermined distance to the left and to the right of a centerline (e.g., two feet to the right of the centerline and two feet to the left of the centerline). During a single repetition, the object is moved back and forth to the starting position. A predetermined number of horizontal displacement repetitions may be performed during the smooth pursuits test (e.g., a total of three horizontal displacement repetitions). During the performance of the test, the object may be displaced at predetermined rate (e.g., the object may be displaced at predetermined rate such that it takes approximately 1.5 to 2.5 seconds to go fully from the left to the right and approximately 1.5 to 2.5 seconds to go fully from the right to the left). Then, during the second part of the test, the subject is instructed again by the clinician to maintain focus on the object as the clinician vertically displaces the object in a smooth manner a predetermined distance above and below a centerline (e.g., two feet above and below the centerline). As for the horizontal displacement portion of the test described above, a predetermined number of vertical displacement repetitions may be performed during the smooth pursuits test (e.g., a total of three vertical displacement repetitions). Also, as explained above for the horizontal displacement portion of the test, the object may be displaced at predetermined rate (e.g., the object may be displaced at predetermined rate such that it takes approximately 1.5 to 2.5 seconds to go fully from the lowest downward position to the highest upward position and approximately 1.5 to 2.5 seconds to go fully from the highest upward position to the lowest downward position). In addition, during the performance of the smooth pursuits test, the following symptoms of the subject may be tracked and recorded by the clinician: (i) headache, (ii) dizziness, (iii) fogginess, and (iv) nausea.

A saccades test evaluates the ability of a subject's eyes to move quickly between targets. During this test, the subject and the clinician may be seated, or the clinician may be standing while the subject is also standing. During horizontal saccades, the clinician holds two horizontally spaced-apart objects (e.g., his or her fingertips) a predetermined distance from the subject (e.g., a distance between two and four feet). Each of the first and second objects is spaced a predetermined horizontal distance from an imaginary centerline between the objects (e.g., two feet to the right of the centerline and two feet to the left of the centerline) so that a predetermined gaze range for the subject is established (e.g., 35 degrees to the left and 35 degrees to the right). During the test, the subject is instructed by the clinician to move his or eyes quickly back and forth from the first object to the second object. During a single repetition, the eyes of the subject are moved back and forth to the starting position. A predetermined number of repetitions may be performed during the horizontal saccades test (e.g., a total of ten repetitions). During the performance of the horizontal saccades test, the following symptoms of the subject may be tracked and recorded by the clinician: (i) headache, (ii) dizziness, (iii) fogginess, and (iv) nausea. During vertical saccades, the clinician holds two vertically spaced-apart objects (e.g., his or her fingertips) a predetermined distance from the subject (e.g., a distance between two and four feet). Each of the first and second objects is spaced a predetermined vertical distance from an imaginary centerline between the objects (e.g., two feet above the centerline and two feet below the centerline) so that a predetermined gaze range for the subject is established (e.g., 35 degrees upward and 35 degrees downward). During the test, the subject is instructed by the clinician to move his or eyes quickly up and down from the first object to the second object. During a single repetition, the eyes of the subject are moved up and down to the starting position. A predetermined number of repetitions may be performed during the vertical saccades test (e.g., a total of ten repetitions). During the performance of the vertical saccades test, the following symptoms of the subject may be tracked and recorded by the clinician: (i) headache, (ii) dizziness, (iii) fogginess, and (iv) nausea.

A near point convergence (NPC) test evaluates the ability of a subject's eyes to view a near target without convergence. During this test, the subject may be standing on the force measurement assembly 102 and wearing his or her corrective lenses, if necessary. The clinician may be standing in front of the subject so that he or she may observe the subject's eye movement during the performance of the test. During the performance of the NPC test, the subject focuses on a small target (e.g., a letter that has approximately 0.2 to 0.25 inches in height) that is spaced approximately an arm's length distance away from the face of the subject. As the NPC test is performed, the subject slowly displaces the small target towards the tip of his or her nose. The subject is instructed to stop displacing the target towards his or her nose when he or she sees two distinct images or the clinician observes an outward deviation of one eye. During the test, the subject is instructed to ignore the blurring of the image. Once the subject has stopped displacing the target towards his or her nose, the distance between the target and the tip of the nose of the subject is measured and recorded. A predetermined number of repetitions of the NPC test may be performed (e.g., a total of three or four repetitions). The measured distance is recorded during each of the repetitions. During the performance of the NPC test, the following symptoms of the subject may be tracked and recorded by the clinician: (i) headache, (ii) dizziness, (iii) fogginess, and (iv) nausea. An abnormal near point of convergence is considered to be greater than or equal to 6 centimeters from the tip of the nose.

A vestibular-ocular reflex (VOR) test evaluates the subject's ability to stabilize vision as the head moves. During this test, the subject may be standing on the force measurement assembly 102. The clinician may be standing in front of the subject so that he or she may observe the subject's eye movement during the performance of the test. During the performance of the VOR test, the subject focuses on a small target (e.g., a letter that has approximately 0.2 to 0.25 inches in height) that is spaced a predetermined distance away from the face of the subject (e.g., a predetermined distance of between two (2) feet and four (4) feet). At the beginning of the VOR test, the clinician holds the small target at a centerline position in front of the subject. During the horizontal VOR test, the subject is instructed to rotate their head horizontally while maintaining focus on the target. In particular, the subject may be instructed to rotate his or her head at a predetermined amplitude (e.g., 20 to 30 degrees) to each side, and a metronome may be used to ensure that the speed of rotation is maintained at a predetermined number of beats per minute (e.g., 180 to 200 beats per minute and/or one beat in each direction). During a single repetition, the head of the subject is moved back and forth to the starting position. A predetermined number of repetitions may be performed during the horizontal VOR test (e.g., a total of ten repetitions). During the performance of the horizontal VOR test, the following symptoms of the subject may be tracked and recorded by the clinician: (i) headache, (ii) dizziness, (iii) fogginess, and (iv) nausea. During the vertical VOR test, the subject displaces his or her head vertically, rather than horizontally. In particular, during the vertical VOR test, the subject may be instructed to rotate his or her head at a predetermined amplitude (e.g., 20 to 30 degrees) up and down, and a metronome may be used to ensure that the speed of rotation is maintained at a predetermined number of beats per minute (e.g., 180 to 200 beats per minute and/or one beat in each direction). During a single repetition, the head of the subject is moved up and down to the starting position. A predetermined number of repetitions may be performed during the vertical VOR test (e.g., a total of ten repetitions). During the performance of the vertical VOR test, the following symptoms of the subject may be tracked and recorded by the clinician: (i) headache, (ii) dizziness, (iii) fogginess, and (iv) nausea.

A visual motion sensitivity (VMS) test evaluates the subject's visual motion sensitivity and the ability to inhibit vestibular-induced eye movements using vision. During this test, the subject may be standing on the force measurement assembly 102 with his or her feet spread apart. The clinician may stand next to and slightly behind the subject, so that the subject is guarded but the subject is able to freely perform the movements during the test. During the test, the subject may hold at least one of his or her arms outstretched while focusing on his or her thumb. Maintaining focus on his or her thumb, the subject rotates, together as a generally single unit, his or her head, eyes, and trunk at a predetermined amplitude to the right and to the left (e.g., at an amplitude between 60 degrees and 80 degrees to the right and to the left). During the performance of the VMS test, a metronome may be used to ensure that the speed of rotation is maintained at a predetermined number of beats per minute (e.g., 50 beats per minutes and/or one beat in each direction). A single repetition is complete when the trunk rotates back and forth to the standing position. A predetermined number of repetitions may be performed during the vertical VMS test (e.g., a total of five repetitions). During the performance of the VMS test, the following symptoms of the subject may be tracked and recorded by the clinician: (i) headache, (ii) dizziness, (iii) fogginess, and (iv) nausea.

In one or more embodiments, the tests performed on the subject 108 may be designed to induce symptoms from the subject 108 (i.e. to push the subject 108 into having particular symptoms, such as those listed in the preceding paragraph) so that the clinician may determine which symptoms become worse during the testing. Also, in these one or more embodiments, while the tests are performed on the subject 108, the induced symptoms may be tracked by the clinician.

Figure 20:
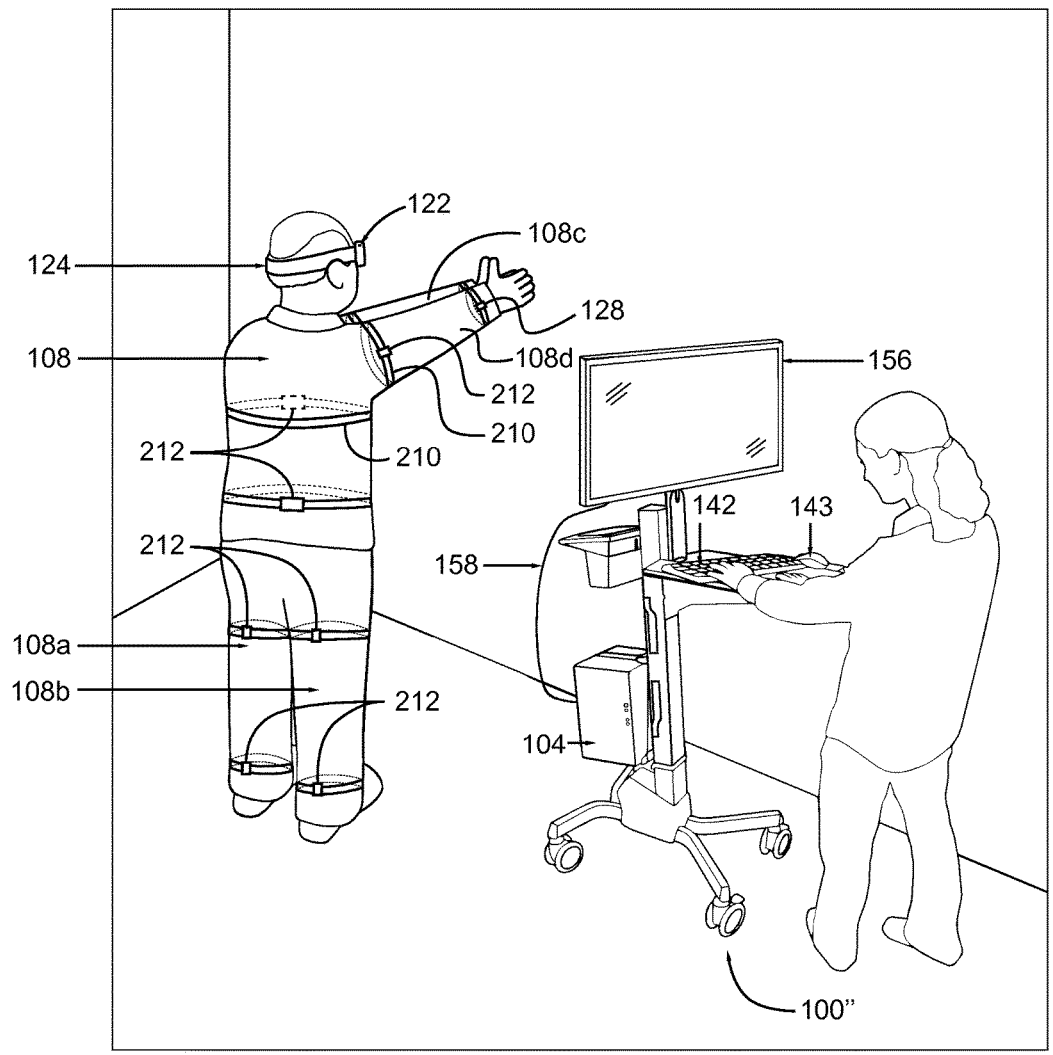
FIG. 20 is a diagrammatic perspective view of a system for measuring postural sway, eye movement and/or eye position, and gaze direction, according to a third embodiment of the invention, wherein the postural sway detection device is in the form of a plurality of inertial measurement units (IMUs)

One alternative embodiment of the system for measuring postural sway, eye movement and/or eye position, and gaze direction is seen generally at 100" in FIG. 20. The system of FIG. 20 is similar in most respects to the system of FIG. 1. However, rather than using a postural sway detection device in the form of the force plate 102 as in FIG. 1, the system of FIG. 20 includes a postural sway detection device in the form of a plurality of inertial measurement units 212 (IMUs 212). As shown in FIG. 20, the subject or patient 108 may be outfitted with a plurality of different inertial measurement units 212 for determining the motion and postural sway of the subject. In the illustrative embodiment, the subject 108 is provided with two (2) inertial measurement units 212 on each of his legs 108a, 108b (e.g., on the side of his legs 108a, 108b). The subject is also provided with two (2) inertial measurement units 212 on each of his arms 108c, 108d (e.g., on the side of his arms 108c, 108d). In addition, the subject 108 of FIG. 20 is provided with an inertial measurement unit 212 around his waist (e.g., with the IMU located on the back side of the subject 108), and another inertial measurement unit 212 around his or her chest (e.g., with the IMU located on the front side of the subject 108 near his sternum). In the illustrated embodiment, each of the inertial measurement units 212 is operatively coupled to the data acquisition/data processing device 104 by wireless means, such as Bluetooth, or another suitable type of personal area network wireless means. Additional details of the IMU hardware and the calculation procedures performed in conjunction with the inertial measurement units 212 will be described hereinafter.

In the illustrated embodiment of FIG. 20, each of the inertial measurement units 212 is coupled to the respective body portion of the subject 108 by a band 210. As shown in FIG. 20, each of the inertial measurement units 212 comprises an IMU housing attached to an elastic band 210. The band 210 is resilient so that it is capable of being stretched while being placed on the subject 108 (e.g., to accommodate the hand or the foot of the subject 108 before it is fitted in place on the arm 108c, 108d or the leg 108a, 108b of the subject 108). The band 210 can be formed from any suitable stretchable fabric, such as neoprene, spandex, and elastane. Alternatively, the band 210 could be formed from a generally non-stretchable fabric, and be provided with latching means or clasp means for allowing the band 210 to be split into two portions (e.g., the band 210 could be provided with a snap-type latching device).

In other embodiments, it is possible to attach the inertial measurement units 212 to the body portions of the subject 108 using other suitable attachment means. For example, the inertial measurement units 212 may be attached to a surface (e.g., the skin or clothing item of the subject 108) using adhesive backing means. The adhesive backing means may comprise a removable backing member that is removed just prior to the inertial measurement unit 212 being attached to a subject 108 or object. Also, in some embodiments, the adhesive backing means may comprise a form of double-sided bonding tape that is capable of securely attaching the inertial measurement unit 212 to the subject 108 or another object.

Figure 21:
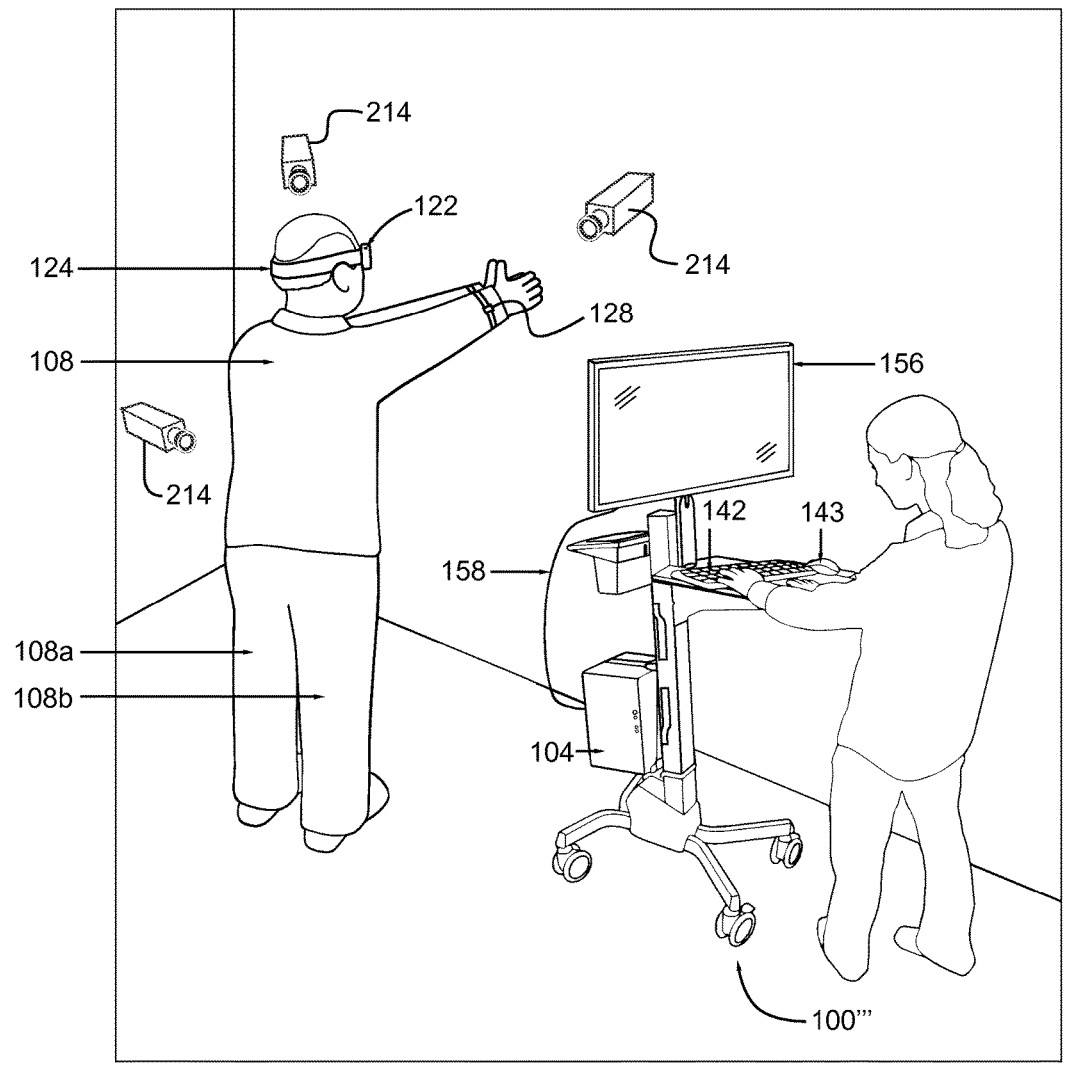
FIG. 21 is a diagrammatic perspective view of a system for measuring postural sway, eye movement and/or eye position, and gaze direction, according to a fourth embodiment of the invention, wherein the postural sway detection device is in the form of a plurality of optical motion capture devices.

Another alternative embodiment of the system for measuring postural sway, eye movement and/or eye position, and gaze direction is seen generally at 100''' in FIG. 21. The system of FIG. 21 is similar in most respects to the systems of FIGS. 1 and 20. However, rather than using a postural sway detection device in the form of the force plate 102 as in the system of FIG. 1, or a postural sway detection device comprising a plurality of inertial measurement units 212 as in the system of FIG. 20, the system of FIG. 21 includes a postural sway detection device in the form of a plurality of optical motion capture devices (i.e., video cameras 214) that capture the motion of the subject so that the postural sway of the subject 108 may be determined therefrom. The video cameras 214 of the optical motion capture system generate motion capture data representative of the captured motion (i.e., video images) of the subject 108. While three (3) cameras 214 are depicted in FIG. 21, one of ordinary skill in the art will appreciate that more or less cameras can be utilized, provided that at least two cameras 214 are used.

The motion capture system illustrated in FIG. 21 is a markerless-type motion detection/motion capture system. That is, the motion capture system of FIG. 21 uses a plurality of high speed video cameras to record the motion of a subject without requiring any markers to be placed on the subject. However, in another embodiment, a marker-based motion capture system is utilized. In this embodiment, the subject is provided with a plurality of markers disposed thereon. These markers are used to record the position of the limbs of the subject in 3-dimensional space. In this embodiment, the plurality of cameras 214 are used to track the position of the markers as the subject moves his or her limbs in 3-dimensional space. For example, the subject may have a plurality of single markers applied to anatomical landmarks (e.g., the iliac spines of the pelvis, the malleoli of the ankle, and the condyles of the knee), or clusters of markers applied to the middle of body segments. As the subject executes particular movements, the data acquisition/data processing device 104 calculates the trajectory of each marker in three (3) dimensions. Then, once the positional data is obtained using the motion capture system, the position of the subject's torso and limbs may be determined, and inverse kinematics may be employed in order to determine the joint angles of the subject. Both of the aforementioned markerless and marker-based motion capture systems are optical-based systems. It is also to be understood that, rather than using an optical motion detection/capture system, a suitable magnetic or electro-mechanical motion detection/capture system can also be employed in the system 100''' described herein.

Figure 22:
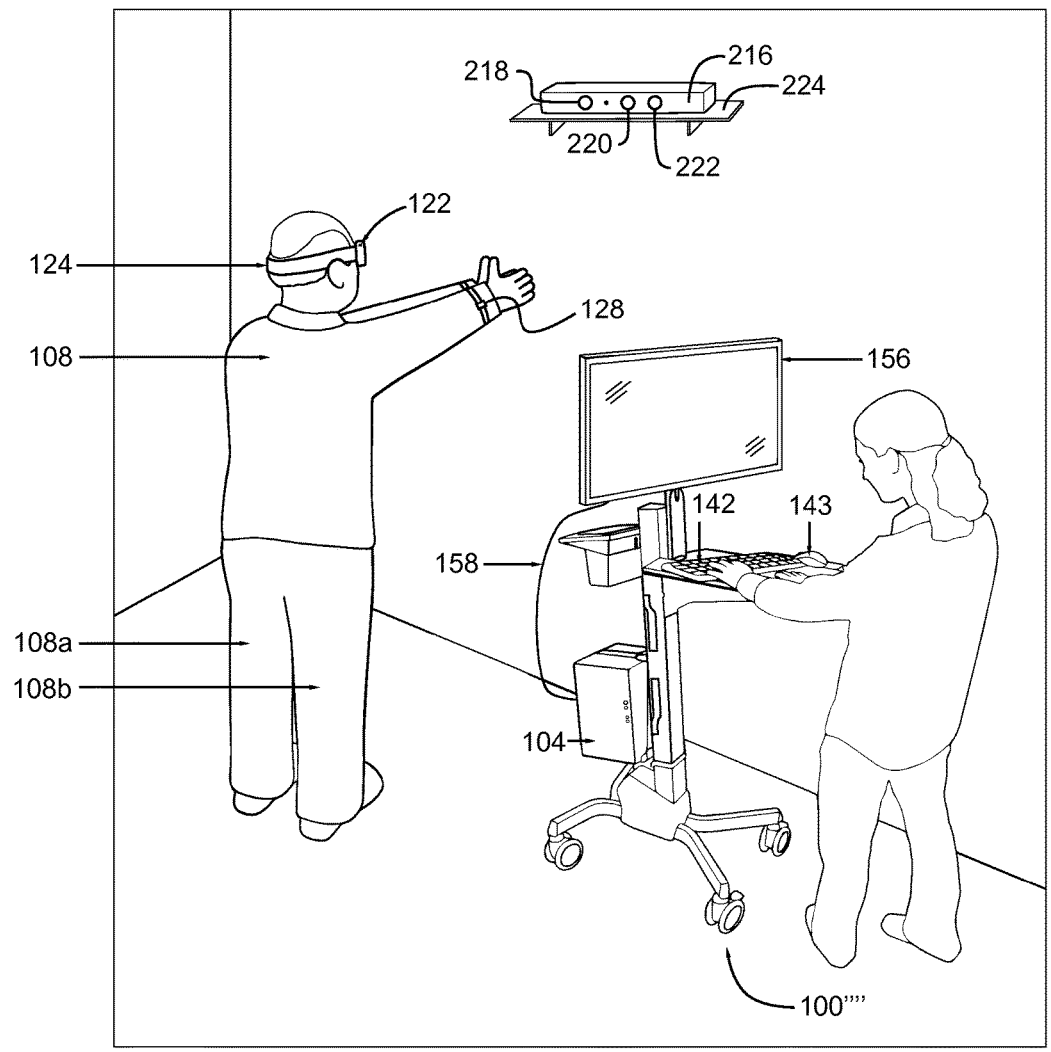
FIG. 22 is a diagrammatic perspective view of a system for measuring postural sway, eye movement and/or eye position, and gaze direction, according to a fourth embodiment of the invention, wherein the postural sway detection device is in the form of an infrared motion capture device.

Yet another alternative embodiment of the system for measuring postural sway, eye movement and/or eye position, and gaze direction is seen generally at 100'''' in FIG. 22. The system of FIG. 22 is similar in most respects to the systems of FIGS. 1, 20, and 21. However, rather than using a postural sway detection device in the form of the force plate 102 as in the system of FIG. 1, a postural sway detection device comprising a plurality of inertial measurement units 212 as in the system of FIG. 20, or postural sway detection device comprising a plurality of optical motion capture devices 214 as in the system of FIG. 21, the system of FIG. 22 includes a postural sway detection device in the form of a motion capture device 216 that employs infrared light to capture the motion of the subject 108 (e.g., the device 216 of FIG. 22 utilizes an infrared (IR) emitter to project a plurality of dots onto objects in a particular space as part of a markless motion capture system). As shown in FIG. 22, a motion capture device 216 with one or more cameras 218, one or more infrared (IR) depth sensors 220, and one or more microphones 222 may be used to provide full-body three-dimensional (3D) motion capture, facial recognition, and voice recognition capabilities. In FIG. 22, it can be seen that the motion capture device 216 may be supported on the wall of the space by means of a shelf 224.

In one or more other embodiments, a method for determining a gaze direction of a subject during a balance test and/or concussion screening test is performed using the system illustrated in FIG. 1. Initially, the eye movement tracking device 124 is positioned on the subject 108 or on an object proximate to the subject 108. In FIG. 1, it can be seen that the eye movement tracking device 124 is in the form of goggles or glasses worn on the head of the subject 108. In addition, the head position detection device 122 is also positioned on the head of the subject 108 or on an object proximate to the head of the subject 108. In the illustrated embodiment of FIG. 1, it can be seen that the head position detection device 122 is integrated into the goggles containing the eye movement tracking device 124 (e.g., the head position detection device 122 may be in the form of an inertial measurement unit (IMU) integrated in the goggles worn by the subject 108). Also, during the performance of the method, at least one limb position detection device 128 is positioned on one or more limbs of the subject 108. For example, in the illustrative embodiment of FIG. 1, an inertial measurement unit (IMU) may be attached to one or both arms of the subject 108. Once the subject has been outfitted with the measurement devices 122, 124, 128, the eye movement and/or eye position of the subject 108 is measured using the eye movement tracking device 124 and the head position of the subject 108 is measured using the head position detection device 122 while at least one of the one or more limbs of the subject 108 and the head of the subject 108 are displaced by the subject 108. In the illustrated embodiment, the head position detection device 122 and the eye movement tracking device 124 may each be operatively coupled to the data acquisition/data processing device 104 by wireless means, such as Bluetooth, or another suitable type of personal area network wireless means.

In one or more embodiments, each inertial measurement unit (e.g., each inertial measurement units 212) may comprise a triaxial (three-axis) accelerometer sensing linear acceleration $\vec{a}'$, a triaxial (three-axis) rate gyroscope sensing angular velocity $\vec{\omega}'$, a triaxial (three-axis) magnetometer sensing the magnetic north vector $\vec{n}'$, and a central control unit or microprocessor operatively coupled to each of accelerometer, gyroscope, and the magnetometer. In addition, each inertial measurement unit may comprise a wireless data interface for electrically coupling the inertial measurement unit to the data acquisition/data processing device 104.

Next, an illustrative manner in which the data acquisition/data processing device 104 of the system 100 in FIG. 1 performs the inertial measurement unit (IMU) calculations will be explained in detail (e.g., for each inertial measurement unit 212). In particular, this calculation procedure will describe the manner in which the orientation and position of one or more body portions (e.g., arms and head) of a subject 108 could be determined using the signals from the plurality of inertial measurement units (IMUs) of the system 100. As explained above, in one or more embodiments, each inertial measurement unit includes the following three triaxial sensor devices: (i) a three-axis accelerometer sensing linear acceleration $\vec{a}'$, (ii) a three-axis rate gyroscope sensing angular velocity $\vec{\omega}'$, and (iii) a three-axis magnetometer sensing the magnetic north vector $\vec{n}'$. Each inertial measurement unit senses in the local (primed) frame of reference attached to the IMU itself. Because each of the sensor devices in each IMU is triaxial, the vectors $\vec{a}'$, $\vec{\omega}'$, $\vec{n}'$ are each 3-component vectors. A prime symbol is used in conjunction with each of these vectors to symbolize that the measurements are taken in accordance with the local reference frame. The unprimed vectors that will be described hereinafter are in the global reference frame.

The objective of these calculations is to find the orientation $\vec{\theta}(t)$ and position $\vec{R}(t)$ in the global, unprimed, inertial frame of reference. Initially, the calculation procedure begins with a known initial orientation $\vec{\theta}_0$ and position $\vec{R}_0$ in the global frame of reference.

For the purposes of the calculation procedure, a right-handed coordinate system is assumed for both global and local frames of reference. The global frame of reference is attached to the Earth. The acceleration due to gravity is assumed to be a constant vector $\vec{g}$. Also, for the purposes of the calculations presented herein, it is presumed the sensor devices of the inertial measurement units (IMUs) provide calibrated data. In addition, all of the signals from the IMUs are treated as continuous functions of time. Although, it is to be understood that the general form of the equations described herein may be readily discretized to account for IMU sensor devices that take discrete time samples from a bandwidth-limited continuous signal.

The orientation $\vec{\theta}(t)$ is obtained by single integration of the angular velocity as follows:

$$\vec{\theta}(t) = \vec{\theta}_0 + \int_0^t \vec{\omega}(t)dt \qquad (17)$$

$$\vec{\theta}(t) = \vec{\theta}_0 + \int_0^t \vec{\Theta}(t)\vec{\omega}'(t)dt \qquad (18)$$

where $\vec{\theta}(t)$ is the matrix of the rotation transformation that rotates the instantaneous local frame of reference into the global frame of reference.

The position is obtained by double integration of the linear acceleration in the global reference frame. The triaxial accelerometer of each IMU senses the acceleration $\vec{a}'$ in the local reference frame. The acceleration $\vec{a}'$ has the following contributors: (i) the acceleration due to translational motion, (ii) the acceleration of gravity, and (iii) the centrifugal, Coriolis and Euler acceleration due to rotational motion. All but the first contributor has to be removed as a part of the change of reference frames. The centrifugal and Euler accelerations are zero when the acceleration measurements are taken at the origin of the local reference frame. The first integration gives the linear velocity as follows:

$$\vec{v}(t) = \vec{v}_0 + \int_0^t \{\vec{a}(t) - \vec{g}\}dt \qquad (19)$$

$$\vec{v}(t) = \vec{v}_0 + \int_0^t \{\vec{\Theta}(t)[\vec{a}'(t) + 2\vec{\omega}' \times \vec{v}'(t)] - \vec{g}\}dt \qquad (20)$$

where $2\vec{\omega}' \times \vec{v}'(t)$ is the Coriolis term, and where the local linear velocity is given by the following equation:

$$\vec{v}'(t) = \vec{\Theta}^{-1}(t)\vec{v}(t) \qquad (21)$$

The initial velocity $\vec{v}_0$ can be taken to be zero if the motion is being measured for short periods of time in relation to the duration of Earth's rotation. The second integration gives the position as follows:

$$\vec{R}(t) = \vec{R}_0 + \int_0^t \vec{v}(t)dt \qquad (22)$$

At the initial position, the IMU's local-to-global rotation's matrix has an initial value $\vec{\Theta}(0) \equiv \vec{\Theta}_0$. This value can be derived by knowing the local and global values of both the magnetic north vector and the acceleration of gravity. Those two vectors are usually non-parallel. This is the requirement for the $\vec{\Theta}_0(\vec{g}', \vec{n}', \vec{g}, \vec{n})$ to be unique. The knowledge of either of those vectors in isolation gives a family of non-unique solutions $\vec{\Theta}_0(\vec{g}', \vec{g})$ or $\vec{\Theta}_0(\vec{n}', \vec{n})$ that are unconstrained in one component of rotation. The $\vec{\Theta}_0(\vec{g}', \vec{n}', \vec{g}, \vec{n})$ has many implementations, with the common one being the Kabsch algorithm. As such, using the calculation procedure described above, the data acquisition/data processing device 104 of the system 100 may determine the orientation $\vec{\theta}(t)$ and position $\vec{R}(t)$ of one or more body portions of the subject 108. For example, the orientation of one or more limbs of the subject 108 (e.g., the orientation of the arms of the subject 108 in FIG. 1) may be determined by computing the orientation $\vec{\theta}(t)$ and position $\vec{R}(t)$ of two points on the limb of the subject 108 (i.e., at the respective locations of two inertial measurement units (IMUs) disposed on the limb of the subject 108).

Figure 23:
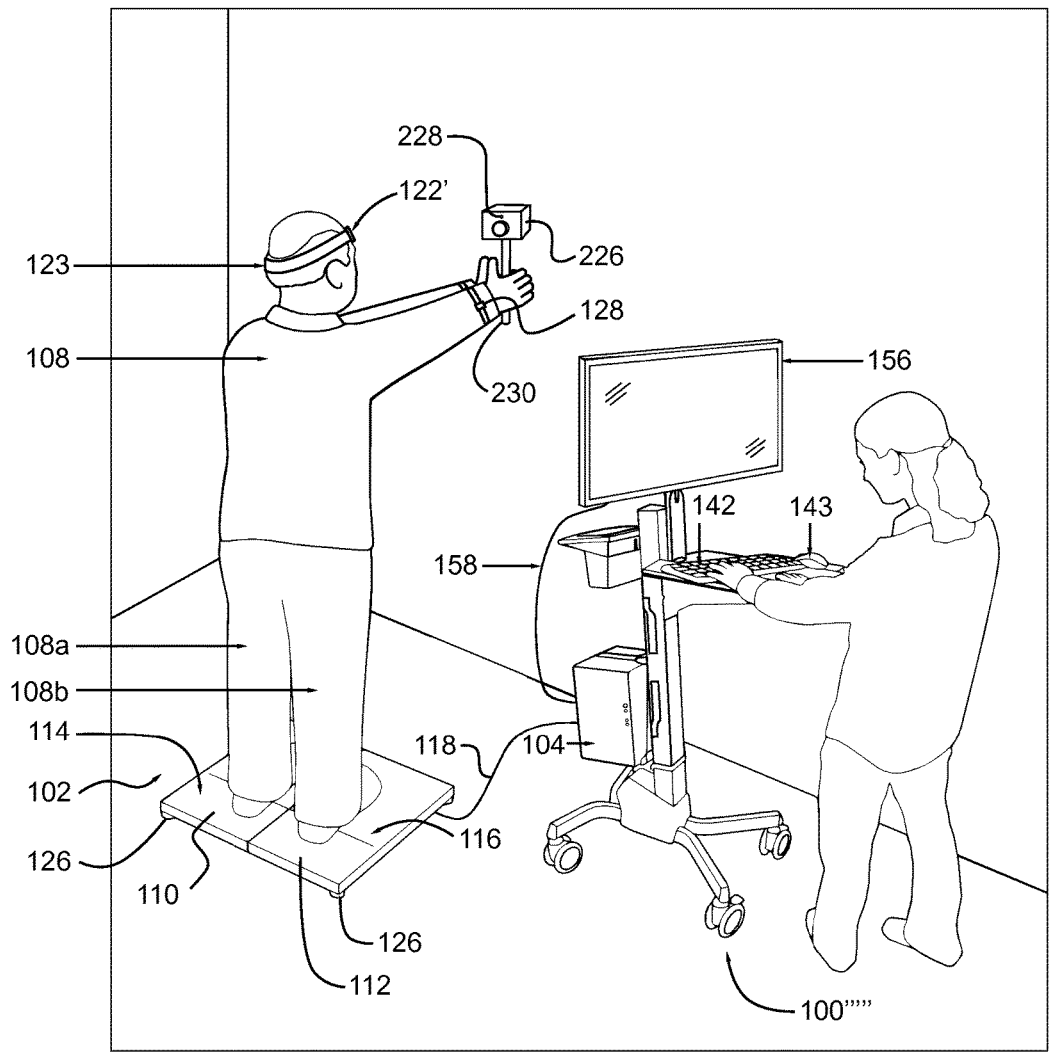
FIG. 23 is a diagrammatic perspective view of a system for measuring postural sway, eye movement and/or eye position, and gaze direction, according to a fifth embodiment of the invention, wherein the eye movement and eye position tracking device is mounted on an elongate handle member that is held by the subject.

In an alternative embodiment, rather than the eye movement tracking device 124 being integrated into goggles or glasses worn on the head of the subject 108, the eye movement tracking device may be in the form of an eye movement tracking device 226 disposed on a graspable object (e.g., an elongate member 230, such as a stick—refer to the system 100'''' of FIG. 23) held in the hands of the subject 108 during the performance of the balance test and/or the concussion screening test. In this alternative embodiment, the eye movement tracking device 226 (e.g., a video camera) may capture the movement and/or position of the subject's eyes while he or she performs the balance test and/or the concussion screening test. Also, as shown in FIG. 23, the eye movement tracking device 226 may comprise a light emitting diode 228 (i.e., an LED 228) disposed thereon so as to provide a target for the subject 108 (i.e., the subject 108 maintains his or her gaze on the LED 228 during the performance of a test). In this alternative embodiment, the head position detection device 122' is still disposed on the head of the subject 108. For example, as shown in the illustrated embodiment of FIG. 23, the head position detection device 122' comprises an inertial measurement unit (IMU) that is attached to the head of the subject 108 via a headband 123.

For example, in the illustrated embodiment of FIG. 1, the eye movement, the eye position, and the head position of the subject 108 are each simultaneously measured while the arms and torso or trunk of the subject 108 are rotated together in a side-to-side manner, and the head of the subject 108 is rotated generally in sync with the arms and trunk of the subject 108. In the illustrative embodiment of FIG. 1, the arms of the subject 108 may be extended outwardly from the torso or trunk of the subject 108 in a generally perpendicular manner from the subject's trunk or torso. When the arms of the subject 108 are extended outwardly from the torso or trunk of the subject 108, the subject 108 may clasp his or her hands together with his or her thumbs pointing generally upwardly from his or her hands. During the simultaneous rotation of the head of the subject 108 and the arms of the subject 108, the subject 108 tries to continually maintain his or her gaze orientation on a portion of his or her hands during arm rotation (e.g., the subject 108 tries to maintain his or her visual focus on his or her upwardly pointed thumbs). In an exemplary embodiment, the subject 108 may be instructed to displace his or her head and arms over a prescribed angular range (e.g., plus or minus 40 degrees or plus or minus 30 degrees). The actual angular range traversed by the subject 108 may be verified by the head position detection device 122 (e.g., IMU) that is disposed on the head of the subject 108. That is, the head position detection device 122 may output an angular range (e.g., plus or minus 35 degrees) that is achieved during the subject's rotation of his or her head. Alternatively, rather than using the head position detection device 122 disposed on the head of the subject 108, the angular range of movement achieved by the head of the subject 108 may be determined using a visual indicator device (e.g., a light) attached to the head of the subject 108. In this alternative embodiment, a projection of the light beam emitted by the light onto a surface disposed in front of the subject 108 (e.g., a wall) may be used to approximate the angular range of movement achieved by the subject 108. For example, the path of the light beam may be compared to spaced-apart markers disposed on the surface in front of the subject 108 (e.g., the wall) to determine if approximately the correct range of angular movement is being achieved by the subject.

Figure 19A:
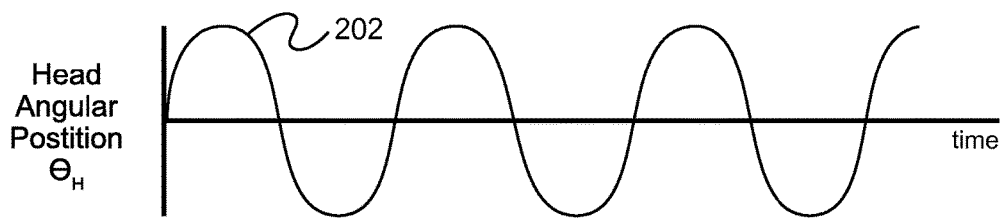
FIG. 19A illustrates an exemplary graph of head angular position for a subject test where the head, torso, and arms of the subject are generally moving in sync with one another and with the target.
Figure 19B:
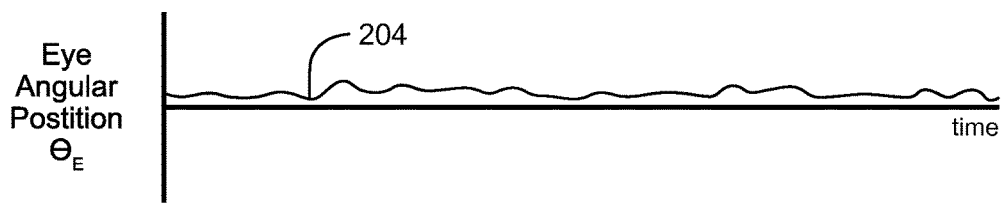
FIG. 19B illustrates an exemplary graph of eye angular position for the subject test where the head, torso, and arms of the subject are generally moving in sync with one another and with the target.
Figure 19C:
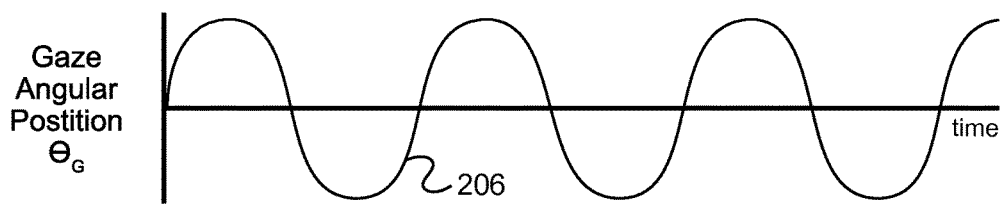
FIG. 19C illustrates an exemplary graph of gaze angular position for the subject test where the head, torso, and arms of the subject are generally moving in sync with one another and with the target.
Figure 19D:
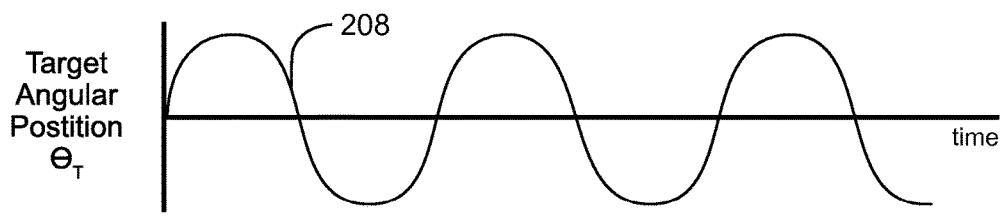
FIG. 19D illustrates an exemplary graph of target angular position for the subject test where the head, torso, and arms of the subject are generally moving in sync with one another and with the target.

Referring to FIGS. 19A-19D, exemplary output results are presented for a balance test and/or the concussion screening test where the subject 108 is simultaneously rotating his or her arms, torso, and head generally in sync with one another (i.e., a test where the subject's head, torso, and outwardly extended arms are generally being displaced in sync with one another). Initially, referring to FIG. 19A, the sinusoidal curve 202 represents the angular position of the subject's head ($\theta_H$) over time (the sinusoidal curve 202 is indicative of the oscillatory motion of the subject's head where the subject's head is rotated back and forth within an angular range, e.g., −30 degrees to 30 degrees). Then, as shown in FIG. 19B, the curve 204 represents the angular position of the subject's eye ($\theta_E$) over time (because the head of the subject 108 is generally being rotated with the target, the eyes of the subject 108 do not generally move with respect to the head of the subject 108, as depicted by the curve 204 in FIG. 19B, which is nearly equal to zero over time). Next, as shown in FIG. 19C, because the gaze direction is generally equal to the sum of the head movement and the eye position, and the angular position of the subject's eye ($\theta_E$) is nearly equal to zero during the test, the angular position of the subject's gaze ($\theta_G$) is approximately equal to the angular position of the subject's head ($\theta_H$) during the test (as illustrated by the sinusoidal curve 206 in FIG. 19C, which is almost equal to the head angular position curve 202 in FIG. 19A). Finally, as depicted in FIG. 19D, the sinusoidal curve 208 represents the angular position of the target ($\theta_T$) over time (the sinusoidal curve 208 is indicative of the oscillatory motion of the target where the target is rotated back and forth within an angular range, e.g., −30 degrees to 30 degrees) during the balance test and/or the concussion screening test.

In an alternative embodiment, rather than the subject 108 simultaneously rotating his or her arms, torso, and head in sync with one another during the performance of the balance test and/or the concussion screening test, the subject 108 may rotate his or her head, while the arms of the subject 108 are extended outwardly and stationary, and while a gaze orientation of the subject 108 is maintained on the upwardly pointing thumbs of the hands of the subject's outwardly extending arms. As in the illustrative embodiment described above, the eye movement, the eye position, and the head position of the subject 108 are simultaneously measured while the subject 108 performs the test in accordance with this alternative embodiment (i.e., head rotated, arms stationary, and subject's gaze fixed on the thumbs of the hands).

Figure 18A:
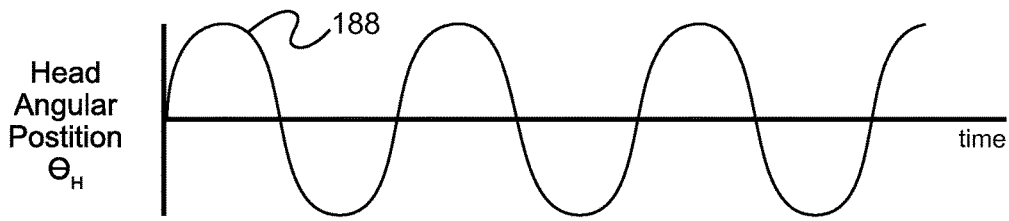
FIG. 18A illustrates an exemplary graph of head angular position for a subject test where the head of the subject is moving, but the torso of the subject and the target are generally stationary.
Figure 18B:
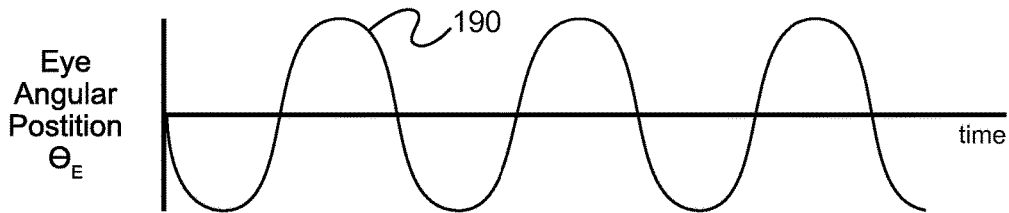
FIG. 18B illustrates an exemplary graph of eye angular position for the subject test where the head of the subject is moving, but the torso of the subject and the target are generally stationary.
Figure 18C:
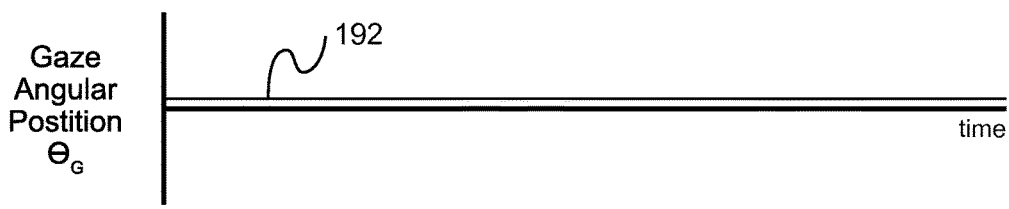
FIG. 18C illustrates an exemplary graph of gaze angular position for the subject test where the head of the subject is moving, but the torso of the subject and the target are generally stationary.
Figure 18D:
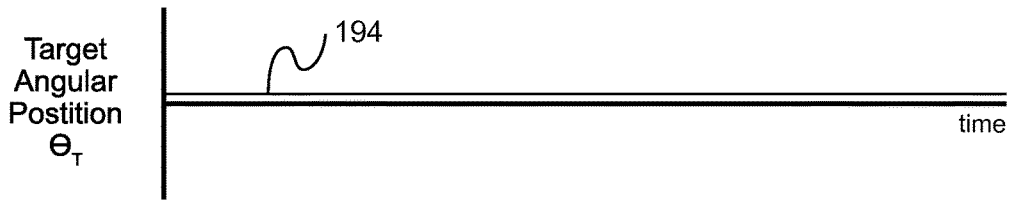
FIG. 18D illustrates an exemplary graph of target angular position for the subject test where the head of the subject is moving, but the torso of the subject and the target are generally stationary.

Referring to FIGS. 18A-18D, exemplary output results are presented for a test where the subject 108 is rotating his or head, while the arms of the subject 108 are extended outwardly and stationary, and while a gaze orientation of the subject 108 is maintained on the upwardly pointing thumbs of the hands of the subject's outwardly extending arms (i.e., a test where the subject's head is moving without the subject's torso and target moving). Initially, referring to FIG. 18A, the sinusoidal curve 188 represents the angular position of the subject's head ($\theta_H$) over time (the sinusoidal curve 188 is indicative of the oscillatory motion of the subject's head where the subject's head is rotated back and forth within an angular range, e.g., −30 degrees to 30 degrees). Then, as shown in FIG. 18B, the sinusoidal curve 190 represents the angular position of the subject's eye ($\theta_E$) over time (the sinusoidal curve 190 is indicative of the oscillatory motion of the subject's eye where the subject's eye is rotated back and forth in a direction that is generally equal and opposite to the motion of the subject's head so that the subject 108 is able to maintain his or her gaze fixed on the stationary target). In other words, the sinusoidal curve 190 in FIG. 18B represents the subject's eye movement with respect to his or her head. Next, as shown in FIG. 18C, because the gaze direction is generally equal to the sum of the head movement and the eye position, and the angular position of the subject's eye ($\theta_E$) is generally equal and opposite to the movement of the subject's head in the illustrative example of FIGS. 18A-18D, the angular position of the subject's gaze ($\theta_G$) is approximately equal to zero (as illustrated by the curve 192 in FIG. 18C). Finally, as depicted in FIG. 18D, because the target is substantially stationary in the illustrative example of FIGS. 18A-18D, the angular position of the target ($\theta_T$) is generally equal to zero (as illustrated by the curve 194 in FIG. 18D).

Also, in an alternative embodiment, rather than performing a visual motion sensitivity-type test wherein the arms, torso, and head of the subject 108 are rotated in sync with one another, the subject may alternatively perform one of the other types of vestibular or ocular motor tests described above in conjunction with the balance test and/or the concussion screening test. In particular, during the balance and/or the concussion screening test, the subject may be instructed to perform any one or more of the following other vestibular or ocular motor tests explained above: (i) a test involving smooth pursuits, (ii) a test involving saccades, (iii) a near point convergence (NPC) test, and (iv) a vestibular-ocular reflex (VOR) test.

During the abovedescribed rotation of at least one of the one or more limbs of the subject 108 and the head of the subject 108, the eye movement tracking device 124 outputs one or more first signals that are representative of the detected eye movement and/or eye position of the subject 108 to the data acquisition/data processing device 104, and the head position detection device 122 outputs one or more second signals that are representative of the detected position of the head of the subject 108 to the data acquisition/data processing device 104. After which, the data acquisition/data processing device 104 is specially programmed to determine one or more gaze directions of the subject 108 from the one or more first signals output by the eye movement tracking device 124 and the one or more second signals output by the head position detection device 122. The data acquisition/data processing device 104 also is specially programmed to determine a position of one or more limbs of the subject 108 from the one or more third signals output by the at least one limb position detection device 128. In addition, the data acquisition/data processing device 104 is further specially programmed to determine whether the one or more gaze directions of the subject 108 that are determined from the one or more first signals and the one or more second signals correspond to a direction in which the one or limbs of the subject 108 are pointed while the at least one of the one or more limbs of the subject 108 and the head of the subject 108 are displaced by the subject 108 during the performance of the balance test and/or the concussion screening test.

Also, in the illustrative embodiment of FIG. 1, it can be seen that the subject 108 is further positioned in an upright position on a force measurement assembly (i.e., the force plate 102) while the at least one of the one or more limbs of the subject 108 and the head of the subject 108 are displaced by the subject 108 during the performance of the balance test and/or the concussion screening test. In particular, the force plate 102 may be used to determine the postural sway of the subject 108 during the performance of the balance test and/or the concussion screening test. That is, the force measurement assembly 102 outputs one or more fourth signals representative of forces and/or moments being applied to the surface 114, 116 of the force measurement assembly 102 by the subject while at least one of the one or more limbs of the subject 108 and the head of the subject 108 are displaced by the subject 108. The data acquisition/data processing device 104 is specially programmed to convert the one or more fourth signals that are representative of the forces and/or moments applied to the surface 114, 116 of the force measurement assembly 102 by the subject into one or more load output values (a combination of force and moments, as described above). After which, the data acquisition/data processing device 104 is specially programmed to compute one or more numerical values (e.g., one or more postural sway angles) that are indicative of a postural stability of the subject 108 by using the one or more load output values (i.e., the computed forces and moments) while at least one of the one or more limbs of the subject 108 and the head of the subject 108 are displaced by the subject 108.

In one or more embodiments, during the performance of the balance test and/or the concussion screening test described above, the data acquisition/data processing device 104 is specially programmed to generate an audio output signal that corresponds to the proper limb and/or head rotation timing of the subject 108, and to output that audio output signal to speakers of the data acquisition/data processing device 104 in order to assist the subject 108 with the proper limb and/or head rotation timing that is required for the balance test and/or the concussion screening test (i.e., a metronome plays from the speakers of the data acquisition/data processing device 104 to assist the subject 108 with the execution of the proper limb and/or head rotation timing). The metronome provides an audible indicator of the pace at which the subject's head and/or limbs should be rotated during the balance test and/or the concussion screening test. As such, the metronome supplements the inertial measurement unit (IMU) or the one or more visual indicators (i.e., light beam emitted from a light source that is rotated between two markers disposed on a wall surface) described above. As such, when the metronome is used, the subject 108 is to rotate in sync with the metronome during the performance of the balance test and/or the concussion screening test. The metronome may emit a predetermined number of beats per minute (e.g., 30 beats per minute, 40 beats per minute, or 50 beats per minute). The exact timing of the metronome will vary based upon the particular subject or patient being tested.

In one or more further embodiments of the invention, a system for measuring the postural sway, eye movement and/or eye position, and gaze direction utilizes a dual-task protocol to assess a medical condition of a subject 108. The first task of the dual-task protocol may comprise a neurocognitive task (i.e. a task which requires a particular mental process), while the second task of the dual-task protocol may comprise a motor or muscular task (i.e. a task which requires the use of muscles of the body). In one or more embodiments, the first cognitive task is performed concurrently with the second motor task so that a subject has to perform both tasks simultaneously.

Figure 8:
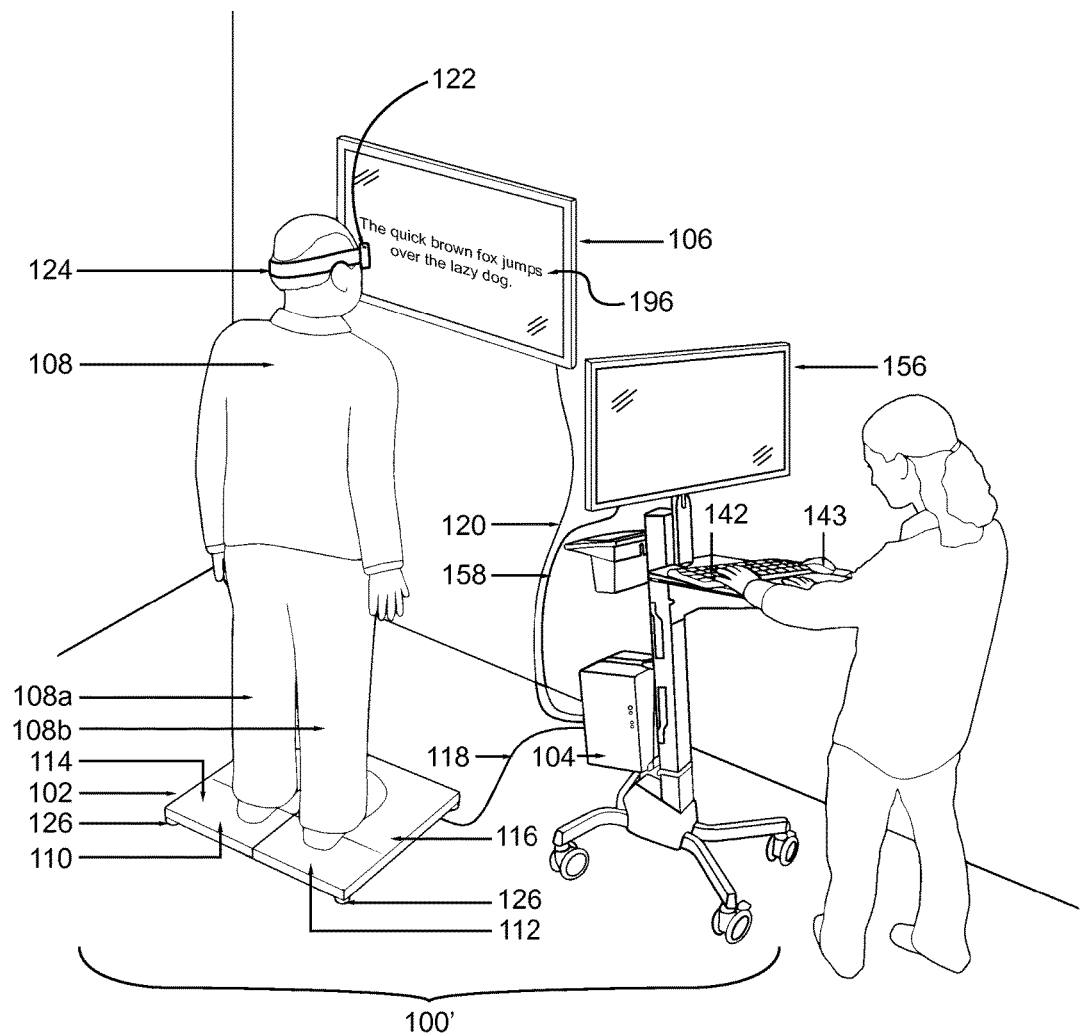
FIG. 8 is a diagrammatic perspective view of a system for measuring postural sway, eye movement and/or eye position, and gaze direction according to a second embodiment of the invention, wherein a visual task of a dual task protocol is being displayed on the subject visual display device.

An exemplary embodiment of a system for performing a dual task protocol is seen generally at 100' in FIG. 8. The system of FIG. 8 is generally the same as the system 100 described above, which is used for measuring the postural sway, eye movement and/or eye position, and gaze direction of a subject 108. For example, like the system 100 described above, the system 100' in FIG. 8 generally comprises a force measurement assembly 102 that is operatively coupled to a data acquisition/data processing device 104 (i.e., a computing device that is capable of collecting, storing, and processing data), which in turn, is operatively coupled to an eye movement and eye position tracking device 124, and an operator visual display device 156. However, unlike the system 100 of FIG. 1, the system of FIG. 8 additionally includes a subject visual display device 106, as well as the operator visual display device 156. Advantageously, providing two visual display devices 106, 156, allows both the subject 108 and the clinician to have dedicated visual display devices (e.g., content for the subject 108 may be displayed on the subject visual display device 106, while the subject's performance is observed by the clinician on the operator visual display device 156).

Figure 9:
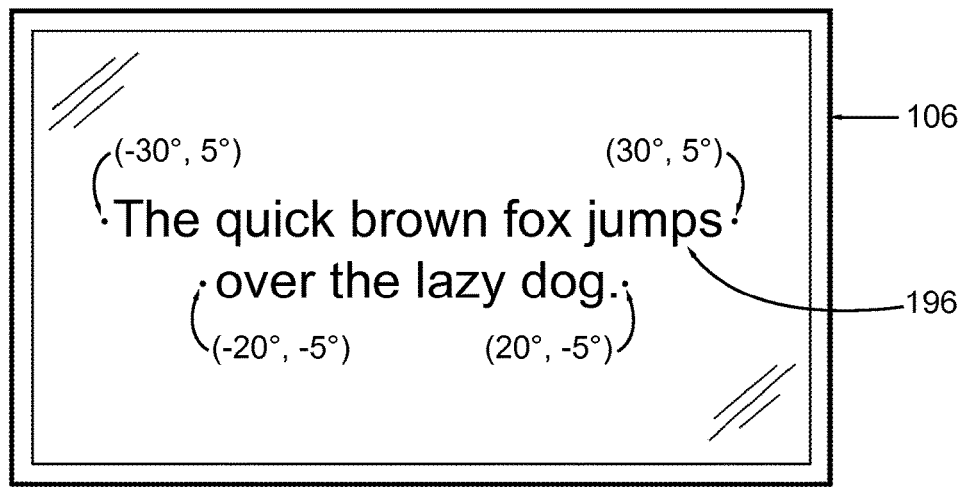
FIG. 9 is a diagrammatic frontal view of the subject visual display device of the system of FIG. 8 with a first exemplary visual task displayed thereon, wherein a passage for the subject to read is displayed on the screen, according to an embodiment of the invention.

With reference to FIGS. 8 and 9, the subject visual display device 106 of the dual task assessment system 100' will be described in more detail. In the illustrated embodiment, like the operator visual display device 156, the subject visual display device 106 is also in the form of a flat panel monitor. Also, similar to the operator visual display device 156, the subject visual display device 106 is operatively coupled to the data acquisition/data processing device 104 by means of a data transmission cable 120. As described above for the operator visual display device 156, those of ordinary skill in the art will readily appreciate that various types of flat panel monitors having various types of data transmission cables 120 may be used to operatively couple the subject visual display device 106 to the data acquisition/data processing device 104. For example, the flat panel monitor employed may utilize a video graphics array (VGA) cable, a digital visual interface (DVI or DVI-D) cable, a high-definition multimedia interface (HDMI or Mini-HDMI) cable, or a DisplayPort digital display interface cable to connect to the data acquisition/data processing device 104. Alternatively, in other embodiments of the invention, the subject visual display device 106 can be operatively coupled to the data acquisition/data processing device 104 using wireless data transmission means. As explained above for the operator visual display device 156, electrical power is supplied to the subject visual display device 106 using a separate power cord that connects to a building wall receptacle.

Those of ordinary skill in the art will appreciate that the subject visual display device 106 can be embodied in various forms. For example, if the subject visual display device 106 is in the form of a flat screen monitor as illustrated in FIG. 8, it may comprise a liquid crystal display (i.e., an LCD display), a light-emitting diode display (i.e., an LED display), a plasma display, a projection-type display, or a rear projection-type display. Although, it will be appreciated that the subject visual display device 106 may take other forms as well, such as a head-mounted display, a heads-up display, or a 3-dimensional display. The subject visual display device 106 may also be in the form of a touch pad display.

In the dual task protocol, the first neurocognitive task may comprise a variety of different cognitive tasks. For example, the neurocognitive task could require the subject to read one or more passages on a visual display device, identify different colors, and identify different letters, numbers, and/or symbols, or a pattern of different letters, numbers, and/or symbols displayed on the subject visual display device 106. One of ordinary skill in the art will readily appreciate that these are merely exemplary neurocognitive tasks, and that other suitable neurocognitive tasks may be employed in conjunction with the claimed invention.

In the illustrative embodiment of FIGS. 8 and 9, the first neurocognitive task requires the subject 108 to read a particular passage 196 displayed on the subject visual display device 106. While the subject is reading the passage 196 displayed on the subject visual display device 106, the eye movement and eye position of the subject 108 is tracked using the eye movement and eye position tracking device 124.

In the illustrative embodiment of FIGS. 8 and 9, as the subject 108 reads the passage 196 on the visual display device 106, the eye movements of the subject 108 are measured using the eye movement and eye position tracking device 124, while the head movements of the subject 108 are measured using the head position detection device 122. In the illustrated embodiment, the data acquisition/data processing device 104 may be specially programmed to compare the eye movements of the subject 108 to the head movements of the subject 108 in order to determine if they are generally equal and opposite to one another. For a normal subject, the head and eye movement tracings are approximately equal to one another in magnitude, but opposite in direction. If the head and eye movements of the tested subject 108 are not approximately equal in magnitude and opposite in direction, then the visual acuity of the subject will deteriorate and the subject 108 will not be able to read the passage 196 displayed on the subject visual display device 106. The data acquisition/data processing device 104 may be specially programmed to determine the amount of deviation between the subject's head and eye movements, and to further determine if the subject 108 has lost visual acuity as a result of the deviation between the subject's head and eye movements exceeding a predetermined deviation value. Also, during the testing, the general reading ability of the subject 108 (i.e., the ability to correctly read the passage 196 on the screen) may be assessed by the clinician or therapist. That is, during the testing, the subject 108 reads the passage 196 on the subject visual display device 106, and the clinician or therapist determines whether or not the subject 108 read the passage 196 correctly or not (e.g., by assigning a reading score to the subject 108). The data acquisition/data processing device 104 may be specially programmed to receive and process this manual reading score for the subject 108, and to incorporate it into the overall computed test score for the subject 108.

In an alternative embodiment, as the subject 108 reads the passage 196 on the visual display device 106 (see FIGS. 8 and 9), the angular eye position of the subject 108 may be compared to the position of the text in the passage 196 on the screen of the visual display device 106 to determine if the subject's reading pattern is normal. Initially, the data acquisition/data processing device 104 may be specially programmed to determine a position of the text on the screen of the visual display device 106. For example, the position of the text on the screen may be defined in terms of pixel coordinates (x pixels by y pixels), which in turn, may be transformed into angular position coordinates (e.g., as shown in the screen image 162 of FIG. 14) so that the position of the text may be compared to the angular eye position of the subject 108. For example, referring to FIG. 9, the starting center point of the first line of the passage 196 in FIG. 9 may correspond to an angular position of (−30°, 5°) while the ending center point of the first line of the passage 196 in FIG. 9 may correspond to an angular position of (30°,5°). The starting center point of the second line of the passage 196 in FIG. 9 may correspond to an angular position of (−20°,−5°) while the ending center point of the second line of the passage 196 in FIG. 9 may correspond to an angular position of (20°,5°). As such, taking the first line of the passage 196 as an example, if the subject 108 is reading the text in a normal manner, his or her eyes should begin at an angular position generally corresponding to (−30°, 5°) and then the x coordinate of the eye position should gradually increase from −30° to 30° as the subject reads from left to right and reaches the end of the first line of text. While reading the first line of the passage 196, the y coordinate of the eye position for the subject 108 should remain generally constant at an angular position of 5°. However, if the subject 108 has a disorder, the x coordinate of the subject's eye position may not consistently increase from −30° to 30° over time. Rather, if the subject 108 is having difficulty reading the passage 196 in FIG. 9, the x coordinate of the subject's eye position may erratically increase and decrease. In addition, if the subject 108 has a disorder that impairs his or reading ability, the y coordinate of the eye position for the subject 108 may not remain generally constant at an angular position of 5°, but rather may oscillate above and below the y coordinate position of the first line of text (e.g., oscillate between 0° and 10°, etc.).

In another embodiment, the first neurocognitive task requires the subject 108 to identify a letter, number, and/or symbol, or a pattern of letters, numbers, and/or symbols displayed on the subject visual display device 106. For example, the optotype "E" may be displayed on the screen of the subject visual display device 106, and the subject 108 may be asked to identify the direction of the optotype "E" on the screen (i.e., identify whether the optotype "E" is pointing up, pointing down, pointing to the left, or pointing to the right). While the subject is identifying the letters, numbers, and/or symbols, or a pattern of letters, numbers, and/or symbols displayed on the subject visual display device 106, the eye movement and eye position of the subject 108 is tracked using the eye movement and eye position tracking device 124.

In yet another embodiment, the first neurocognitive task requires the subject 108 to follow a moving target on the screen of the subject visual display device 106 while the eye movement and eye position tracking device 124 is used to track the angular position of the subject's eyes. In this embodiment, the data acquisition/data processing device 104 is specially programmed to assess the ability of the subject 108 in tracking the moving target with his or her eyes. The performance of the subject 108 during this test may be quantified using (i) an eye pursuit performance parameter specifying an amount that one or more eyes of the subject lag behind an intended target, (ii) an eye velocity of one or more eyes of the subject, (iii) an eye pursuit performance ratio of eye velocity to target velocity for the subject, (iii) an accuracy parameter specifying an accuracy of one or more eyes of the subject, and (iv) an eye latency parameter specifying a time for the subject to initiate eye movements.

In one or more embodiments, it is to be understood that various performance assessment parameters may be used to assess a subject's performance during the execution of the neurocognitive tasks set forth above. For example, one or more of the following performance parameters may be used to assess the subject's performance during the first task: (i) an eye pursuit performance parameter specifying an amount that one or more eyes of the subject lag behind an intended target, (ii) an eye velocity of one or more eyes of the subject, (iii) an eye pursuit performance ratio of eye velocity to target velocity for the subject, (iii) an accuracy parameter specifying an accuracy of one or more eyes of the subject, and (iv) an eye latency parameter specifying a time for the subject to initiate eye movements. In some embodiments, all of the aforementioned performance parameters (i), (ii), (iii), and (iv) may be used to assess the subject's performance during the first task.

Similarly, the second motor task may comprise a variety of different motor or muscular tasks, which are performed on the surface(s) of the force measurement assembly 102 (e.g., the dual force plate in FIG. 8). For example, the motor or muscular task could require the subject to maintain a substantially stationary, upright position on the force measurement surface(s), or balance one or more objects while disposed on the force measurement surface(s) (e.g., balancing a tray with empty cups or cups filled with water disposed thereon). Similar to that which was described above for the cognitive tasks, one of ordinary skill in the art will readily appreciate that these are merely exemplary motor tasks, and that other suitable motor tasks may be employed in conjunction with the claimed invention.

In addition, it is to be understood that various performance assessment parameters may be used to assess a subject's performance during the execution of the motor or muscular tasks set forth above. For example, one or more of the following performance parameters may be used to assess the subject's performance during the second task: (i) a maximum sway range of the center of pressure of a force vector applied by the subject on the measurement assembly 102, (ii) a maximum sway range of the center of gravity of the subject 108, and (iii) a confidence area for a path of the subject's center of pressure. In some embodiments, all of the aforementioned performance parameters (i), (ii), and (iii) may be used to assess the subject's performance during the second task.

As an alternative to, or in addition to the neurocognitive test, the subject also may perform one of the other types of vestibular or ocular motor tests described above in conjunction with the dual task protocol. In particular, as part of the dual task protocol, the subject may be instructed to perform any one or more of the following other vestibular or ocular motor tests explained above: (i) a test involving smooth pursuits, (ii) a test involving saccades, (iii) a near point convergence (NPC) test, (iv) a vestibular-ocular reflex (VOR) test, and (v) a visual motion sensitivity (VMS) test.

Initially, in the illustrative embodiment, at the beginning of the dual-task protocol, the subject 108 is positioned on the force measurement assembly (102, 102'). If the dual force plate assembly 102 is utilized for the dual-task protocol, the feet of the subject 108 will be placed on respective first and second measurement surfaces 114, 116. In contrast, if the single force plate 102' is used for the dual-task protocol, both feet of the subject will be placed on the single measurement surface of the force plate 102'. Next, a scene is displayed on the subject visual display device 106 that relates to the performance of the first neurocognitive task. For example, if the neurocognitive task requires the subject 108 to read a particular passage, the subject 108 is presented with one or more lines of text to read on the subject visual display device 106. Also, the subject 108 is instructed to perform the second motor task. As an example, the second motor or muscular task may require the subject to maintain a substantially stationary, upright position on the force measurement surfaces 114, 116 of the force measurement assembly 102. Advantageously, during the execution of the dual task protocol by the subject, the force measurement assembly 102 is used to: (i) determine the subject's performance of the motor task and/or (ii) if the motor task requires a certain movement to be executed by the subject, verify that the motor task is actually being performed by the subject (i.e., to verify that the subject is not just focusing on the neurocognitive task and skipping the motor task). In other words, during the dual task protocol, the force measurement assembly 102 is used in an analytical manner. While the subject performs the motor task, the force transducers of the force measurement assembly 102 are used to sense the forces and/or moments that are applied to the surface of the force measurement assembly 102 by the subject. The signals from the force transducers of the force measurement assembly 102 are transmitted to the data acquisition/data processing device 104, and the data acquisition/data processing device 104 computes one or more numerical values (e.g., the subject's center of pressure or center of gravity) from the signals.

In one or more embodiments, the force measurement assembly 102 is in the form of a static force plate (i.e., the force plate surface is stationary and is not displaced relative to the floor or ground). Such a static force plate does not have any actuators or other devices that translate or rotate the force measurement surface. In one or more alternative embodiments, the force measurement assembly 102 is in the form of a dynamic force plate (i.e., the force plate surface is displaced and/or translated relative to the floor or ground). As such, a dynamic force plate contains one or more actuators or other devices that are capable of translating and/or rotating the force plate surface.

In the one or more embodiments, the data acquisition/data processing device 104 is specially programmed to compute the center of gravity (COG) for the subject 108 using the procedures described above (i.e., approximation from the center of pressure (COP) using a Butterworth filter, or direct computation of the center of gravity (COG)).

Then, the movements of the subject 108 are measured using the force measurement assembly 102 in FIG. 8. The force measurement assembly 102 outputs the one or more first signals that are generated based upon the one or more detectable movements on the surface 114, 116 of the force measurement assembly 102. In addition, the eye movement and eye position of the subject 108 is measured using the eye movement tracking device 124, while one or more detectable movements of the subject 108 are simultaneously measured by the force measurement assembly 102. The eye movement tracking device 124 outputs one or more second signals that are representative of the detected eye movement and eye position of the subject 108 to the data acquisition/data processing device 104. After which, the data acquisition/data processing device 104 is specially programmed to compute one or more numerical values from the one or more first signals output by the force measurement assembly 102. The data acquisition/data processing device 104 also is specially programmed to determine one or more changes in eye position of the subject 108 from the one or more second signals output by the eye movement tracking device 124.

After the data acquisition/data processing device 104 computes the one or more numerical values from the one or more first signals outputted by the force measurement assembly 102 and determines the one or more changes in eye position of the subject from the one or more second signals output by the eye movement tracking device 124, the data acquisition/data processing device 104 may be specially programmed to quantitatively determine a subject's performance during the first and second tasks. The assessment of the subject's performance of the first task being based at least partially upon the one or more changes in eye position of the subject computed from the signals of the eye movement and eye position tracking device 124. The assessment of the subject's performance of the second motor task is based at least partially upon the one or more numerical values computed from the signals of the force measurement assembly 102. The subject's performance of the first cognitive task is quantitatively expressed in terms of one or more first performance values, while the subject's performance of the second task is quantitatively expressed in terms of one or more second performance values.

Finally, a medical condition of the subject 108 is assessed by using at least one of the one or more first and second performance values (i.e., one or more numerical scores). For example, in one or more embodiments, an inability to properly follow words in the passage 196 of FIGS. 8 and 9 with one's eyes and a large sway range determined by the force measurement assembly may be associated with a particular medical condition. In one or more embodiments, one or more changes in eye position of the subject's eye, as determined from the eye movement and eye position tracking device 124, and/or one or more numerical postural sway values, as determined from the force measurement assembly 102, 102', may be used to predict if a subject 108 has a particular medical condition. In one or more embodiments, one or more of the following medical conditions may be assessed using at least one of the one or more first and second performance values: (i) a traumatic brain injury (TBI) or concussion, (ii) a neurological disorder or disease, and (iii) a muscular disorder or disease.

In one or more embodiments, the data acquisition/data processing device 104 may further be specially programmed to combine the first performance value with the second performance value to obtain an overall combined score for assessing the medical condition of the subject 108. For example, a first performance value for the subject 108 may comprise a measurement of how far behind the eyes lag a target (e.g., 10 degrees) that is moving on the screen of the subject visual display device 106. In an exemplary embodiment, a second performance value for the subject 108 may comprise one of the following: (i) a maximum sway of center-of-pressure (COP) (e.g., plus or minus 15 millimeters), (ii) a maximum sway of center-of-gravity (COG) about the ankle (e.g., plus or minus 7 degrees), and (iii) an area of ellipse fitted around the path of the COP with, for example, a 90 percent confidence area (e.g., 4.0 sq. centimeters). Considering the above examples, an overall combined score for assessing the medical condition of the subject 108 may comprise one of the following: (i) a first performance value of 10 degrees multiplied by a second performance value of 15 millimeters so as to obtain an overall combined score of 150 (i.e., 10×15), (ii) a first performance value of 10 degrees multiplied by a second performance value of 7 degrees so as to obtain an overall combined score of 70 (i.e., 10×7), and (iii) a first performance value of 10 degrees multiplied by a second performance value of 4.0 sq. centimeters so as to obtain an overall combined score of 40 (i.e., 10×4.0), depending on which of the above balance scoring techniques is utilized. The final score result(s) may be compared with the score for a normal subject. When one or more of the individual scores or their product (as illustrated above) is not normal, this may be indicative of a particular medical condition.

In addition, the data acquisition/data processing device 104 may be specially programmed to determine whether or not a subject 108 has a particular medical condition (e.g., a traumatic brain injury (TBI) or concussion) by testing the subject 108 before and after a particular event has occurred. For example, on day 1, prior to engaging in any athletic activities involving substantial contact with other players or another object (e.g., football or ice hockey), a first subject 108 is tested several times using the system 100' of FIG. 8, and has a mean first performance value of 5 degrees (i.e., an angular measurement of how far behind the eyes lag the target) for the neurocognitive task after being tested for three trials thereof, and a mean second performance value of plus or minus 3 degrees (i.e., a maximum sway of center-of-gravity (COG) about the ankle) for the motor or muscular task after being tested for three trials thereof, resulting in an overall combined score of 15 (i.e., 5×3). Subsequently, on day 30, after playing football, and sustaining a severe impact to the head during a tackle, the same first subject is again tested on the system 100' of FIG. 8. However, on day 30, the first subject has an increased mean first performance value of 15 degrees for the neurocognitive task after being tested for three trials thereof, and an increased mean second performance value of plus or minus 10 degrees for the motor or muscular task after being tested for three trials thereof, resulting in an overall combined score of 150 (i.e., 15×10). Based upon a comparison of the initial average combined score of 15 to the subsequent average combined score of 150, the data acquisition/data processing device 104 of the system 100' of FIG. 8 determines that the first subject has "Possibly Sustained a Concussion".

As another example, on day 1, prior to engaging in any athletic activities involving substantial contact with other players or another object (e.g., football or ice hockey), a second subject 108 is tested several times using the system 100' of FIG. 8, and has a mean first performance value of 8 degrees (i.e., an angular measurement of how far behind the eyes lag the target) for the neurocognitive task after being tested for three trials thereof, and a mean second performance value of plus or minus 6 degrees (i.e., a maximum sway of center-of-gravity (COG) about the ankle) for the motor or muscular task after being tested for three trials thereof, resulting in an overall combined score of 48 (i.e., 8×6). Subsequently, on day 45, after playing ice hockey, and sustaining a blow to the head from an opponent's hockey stick, the same subject is again tested on the system 100' of FIG. 8. However, on day 45, the second subject has only a slightly increased mean first performance value of 9 degrees for the neurocognitive task after being tested for three trials thereof, and a slightly decreased mean second performance value of plus or minus 5 degrees for the motor or muscular task after being tested for three trials thereof, resulting in an overall combined score of 45 (i.e., 9×5). Based upon a comparison of the initial average combined score of 48 to the subsequent average combined score of 45, the data acquisition/data processing device 104 of the system 100' of FIG. 8 determines that the subject "Does Not Readily Appear to Have Sustained a Concussion". In some instances, the data acquisition/data processing device 104 may also conclude that it is "Indeterminable Whether or Not Subject Has Sustained a Concussion" (e.g., when scores achieved by the subject are too erratic). At the conclusion of the testing, the predicted medical condition evaluation of the subject is outputted to the subject visual display device 106 and/or the operator visual display device 156 so that the subject and/or the clinician can be informed of whether or not the subject appears to have a particular medical condition.

In one or more embodiments of the invention, a series of tests are performed in conjunction with the dual-task protocol. For example, in one such variation, the subject initially will be asked to perform a neurocognitive task (e.g., reading a particular passage that is displayed on the subject visual display device 106). Next, the subject will be instructed to perform a motor/muscular task (e.g., balancing a tray with empty cups or cups filled with water disposed thereon). Finally, the subject will be asked to perform both the cognitive task and the motor/muscular task simultaneously (i.e., the performance of dual tasks). Moreover, the results during each of the tests can also be compared to the results from a baseline test (i.e., results generated during tests that were performed before the subject 108 had experienced the medical condition being assessed, when the subject was considered healthy).

In addition, in an alternative embodiment, a pressure measurement assembly or a contact/timing measurement assembly (e.g., a contact mat with time measurement capabilities) may be used in lieu of the force measurement assemblies 102, 102'. For example, in these alternative embodiments, the force transducers 160 disposed underneath the top plates may be replaced with pressure transducers in the case of a pressure measurement assembly, and may be replaced with contact or timing switches in the case of a contact/timing measurement assembly. Pressure measurement assemblies could be used to output the subject's foot pressure distribution and/or force and pressure time integrals computed using the subject's foot pressure distribution. Contact/timing measurement assemblies (e.g., contact mats), if substituted for each of the force measurement assemblies 102, 102', could be used to output the time duration between the subject's successive contact periods with the mat surface. As such, the rhythm and timing of the subject could be determined during the performance of the motor task so that it could be determined whether or not the motor task was being properly performed by the subject.

In one or more embodiments of the invention, the system 100' of FIG. 8 is used to determine a subject's point of failure during the dual task protocol and/or determine the task during which the subject's failure occurs (e.g., a failure occurs during the neurocognitive task or the motor task). For example, during the performance of the second motor task, it may be determined that the failure occurs when the subject leans too much while performing the motor task. The subject's inability to perform the motor task without falling may be indicative of muscular disorder. Alternatively, the failure may occur during the performance of the neurocognitive task, which may be indicative of a cognitive disorder. Advantageously, once the subject's deficiency or deficiencies are identified, the appropriate corrective measures can be taken (e.g., if the failure occurred during the motor task, measures can be taken to treat the muscular disorder).

It is readily apparent that the embodiments of the system 100, 100' for measuring eye movement and/or eye position and postural sway of a subject described above offer numerous advantages and benefits. These same advantages and benefits are realized by the methods that utilize the system 100, 100'. In particular, the systems and methods discussed herein, which measure eye movement and/or eye position and postural sway of a subject, enable head, eye, and postural movements to be quantitatively evaluated during head-eye coordination exercises. Moreover, the systems and methods described herein enable a patient's functional status to be objectively documented before, during, after therapy. Furthermore, the systems and methods discussed herein, which measure eye movement and/or eye position and postural sway of a subject, enable a medical condition to be assessed (e.g., a traumatic brain injury (TBI) or concussion) so that the proper treatment procedures can be implemented. As such, it is readily apparent from the various advantages and benefits described herein that the system 100, 100' for measuring eye movement and/or eye position and postural sway of a subject, and the methods practiced using the system 100, 100', significantly advance the interrelated fields of vision, vestibular, and balance assessment.

Moreover, while reference is made throughout this disclosure to, for example, "one embodiment" or a "further embodiment", it is to be understood that some or all aspects of these various embodiments may be combined with one another as part of an overall embodiment of the invention. That is, any of the features or attributes of the aforedescribed embodiments may be used in combination with any of the other features and attributes of the aforedescribed embodiments as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A method for concurrently measuring the eye movement or eye position and postural sway of a subject, the method comprising the steps of:

providing an eye movement tracking device configured to track eye movement or eye position of the subject while the subject performs a balance test or a concussion screening test, the eye movement tracking device being configured to output one or more first signals that are representative of the detected eye movement or eye position of the subject;

providing a postural sway detection device, the postural sway detection device configured to detect a postural sway of the subject while the subject performs the balance test or the concussion screening test, the postural sway detection device being configured to output one or more second signals that are representative of the detected postural sway of the subject;

providing at least one limb position detection device, the at least one limb position detection device configured to detect a position of one or more limbs of the subject and output one or more third signals that are representative of the detected position of the one or more limbs of the subject;

providing a data processing device operatively coupled to the eye movement tracking device, the postural sway detection device, and the at least one limb position detection device, the data processing device configured to receive the one or more first signals that are representative of the detected eye movement or eye position of the subject, the one or more second signals that are representative of the detected postural sway of the subject, and the one or more third signals that are representative of the detected position of the one or more limbs of the subject, the data processing device further configured to determine the eye movement or eye position of the subject using the one or more first signals, the postural sway of the subject using the one or more second signals, and the position of the one or more limbs of the subject using the one or more third signals;

positioning the subject in an upright position on a surface;

positioning the at least one limb position detection device on the one or more limbs of the subject between a hand and a shoulder of the subject;

providing a visual target that is a portion of the one or more limbs of the subject;

instructing the subject to displace the one or more limbs while the subject maintains his or her gaze on the visual target;

measuring the eye movement or eye position of the subject using the eye movement tracking device, and outputting the one or more first signals that are representative of the detected eye movement or eye position of the subject from the eye movement tracking device;

measuring the postural sway of the subject using the postural sway detection device while measuring the eye movement or eye position of the subject, and outputting the one or more second signals that are representative of the postural sway of the subject from the postural sway detection device;

measuring the position of the one or more limbs of the subject using the at least one limb position detection device while the one or more limbs of the subject are displaced by the subject, and outputting the one or more third signals that are representative of the detected position of the one or more limbs of the subject from the at least one limb position detection device;

determining, by using the data processing device, eye movement or eye position data for the subject from the one or more first signals output by the eye movement tracking device;

determining, by using the data processing device, the position of the one or more limbs of the subject from the one or more third signals output by the at least one limb position detection device in order to determine the position of the visual target;

determining, by using the data processing device, one or more eye movement deviation values based upon the eye movement or eye position data determined for the subject, the one or more eye movement deviation values quantifying an amount by which one or more eyes of the subject lag behind the visual target during the balance test or the concussion screening test;

determining, by using the data processing device, postural sway data for the subject from the one or more second signals output by the postural sway detection device, wherein the postural sway data determined by the data processing device includes at least one of: (i) a center of pressure for the subject and (ii) a center of gravity for the subject;

determining, by using the data processing device, a balance sway score for the subject based upon the postural sway data determined for the subject; and computing, by using the data processing device, an adjusted balance sway score for the subject by increasing the balance sway score determined for the subject by a numerical factor proportionate to the one or more eye movement deviation values in order to obtain an overall quantitative assessment of performance during the execution of the balance test or the concussion screening test.

2. The method according to claim 1, wherein the eye movement tracking device comprises at least one of the following: (i) a video camera, (ii) an infrared sensor, (iii) an ultrasonic sensor, and (iv) an electrooculographic sensor; and
wherein the step of measuring the eye movement or eye position of the subject using the eye movement tracking device further comprises measuring the eye movement or eye position of the subject using at least one of: (i) the video camera, (ii) the infrared sensor, (iii) the ultrasonic sensor, and (iv) the electrooculographic sensor.

3. The method according to claim 1, wherein the postural sway detection device comprises at least one of the following: (i) a force or balance plate, (ii) one or more inertial measurement units, (iii) an optical motion capture device, and (iv) an infrared motion capture device; and
wherein the step of measuring the postural sway of the subject using the postural sway detection device further comprises measuring the postural sway of the subject using at least one of: (i) the force or balance plate, (ii) the one or more inertial measurement units, (iii) the optical motion capture device, and (iv) the infrared motion capture device.

4. The method according to claim 1, wherein the step of computing, by using the data processing device, an adjusted balance sway score for the subject comprises multiplying the balance sway score determined for the subject by the numerical factor proportionate to the one or more eye movement deviation values in order to obtain the overall quantitative assessment of performance during the execution of the balance test or the concussion screening test.

5. The method according to claim 1, further comprising the step of:
assessing a medical condition of the subject by comparing the adjusted balance sway score for the subject to a baseline score for the subject or to a score for another subject without the medical condition.

6. The method according to claim 1, wherein the at least one limb position detection device comprises at least one inertial measurement unit attached to one of the one or more limbs of the subject.

7. The method according to claim 1, wherein the step of instructing the subject to displace the one or more limbs while the subject maintains his or her gaze on the visual target further comprises instructing the subject to displace the one or more limbs over a prescribed angular range while the subject maintains his or her gaze on the visual target; and
wherein the step of determining the position of the one or more limbs of the subject from the one or more third signals output by the at least one limb position detection device further comprises determining, by using the data processing device, an angular position of the one or more limbs as the subject displaces the one or more limbs over the prescribed angular range.

8. A method for concurrently measuring the eye movement or eye position and postural sway of a subject, the method comprising the steps of:
providing an eye movement tracking device configured to track eye movement or eye position of the subject while the subject performs a balance test or a concussion screening test, the eye movement tracking device being configured to output one or more first signals that are representative of the detected eye movement or eye position of the subject;
providing a postural sway detection device, the postural sway detection device configured to detect a postural sway of the subject and a position of one or more limbs of the subject while the subject performs the balance test or the concussion screening test, the postural sway detection device being configured to output one or more second signals that are representative of the detected postural sway of the subject and the detected position of the one or more limbs of the subject;

providing a data processing device operatively coupled to the eye movement tracking device and the postural sway detection device, the data processing device configured to receive the one or more first signals that are representative of the detected eye movement or eye position of the subject and the one or more second signals that are representative of the detected postural sway of the subject, the data processing device further configured to determine the eye movement or eye position of the subject using the one or more first signals and the postural sway of the subject using the one or more second signals;

positioning the subject in an upright position on a surface;

providing a visual target that is a portion of the one or more limbs of the subject;

instructing the subject to displace the one or more limbs while the subject maintains his or her gaze on the visual target;

measuring the eye movement or eye position of the subject using the eye movement tracking device, and outputting the one or more first signals that are representative of the detected eye movement or eye position of the subject from the eye movement tracking device;

measuring the postural sway of the subject and the position of the one or more limbs of the subject using the postural sway detection device while the one or more limbs of the subject are displaced by the subject and the eye movement or eye position of the subject is measured, and outputting the one or more second signals that are representative of the postural sway of the subject and the detected position of the one or more limbs of the subject from the postural sway detection device;

determining, by using the data processing device, eye movement or eye position data for the subject from the one or more first signals output by the eye movement tracking device;

determining, by using the data processing device, postural sway data for the subject from the one or more second signals output by the postural sway detection device;

determining, by using the data processing device, the position of the one or more limbs of the subject from the one or more second signals output by the postural sway detection device in order to determine the position of the visual target;

determining, by using the data processing device, a first numerical score for the subject based upon the eye movement or eye position data determined for the subject, wherein the first numerical score comprises one or more of the following: (i) an eye pursuit performance parameter specifying an amount that one or more eyes of the subject lag behind the visual target, (ii) an eye pursuit performance ratio of subject eye velocity to visual target velocity, and (iii) an eye latency parameter specifying a time for the subject to initiate eye movements in response to the movement of the visual target;

determining, by using the data processing device, a second numerical score for the subject based upon the postural sway data determined for the subject;

combining, by using the data processing device, the first numerical score with the second numerical score to obtain an overall combined sway and eye movement score for the subject, wherein combining the first numerical score with the second numerical score to obtain the overall combined sway and eye movement score for the subject comprises computing, by using the data processing device, a multiplicative product between the first numerical score and the second numerical score; and assessing a performance of the subject by comparing the overall combined sway and eye movement score for the subject to a baseline score for the subject or to a score for another subject.

9. The method according to claim 8, wherein the eye movement tracking device comprises at least one of the following: (i) a video camera, (ii) an infrared sensor, (iii) an ultrasonic sensor, and (iv) an electrooculographic sensor; and wherein the step of measuring the eye movement or eye position of the subject using the eye movement tracking device further comprises measuring the eye movement or eye position of the subject using at least one of: (i) the video camera, (ii) the infrared sensor, (iii) the ultrasonic sensor, and (iv) the electrooculographic sensor.

10. The method according to claim 8, wherein the postural sway detection device comprises at least one of the following: (i) one or more inertial measurement units, (ii) an optical motion capture device, and (iii) an infrared motion capture device; and wherein the step of measuring the postural sway of the subject using the postural sway detection device further comprises measuring the postural sway of the subject using at least one of: (i) the one or more inertial measurement units, (ii) the optical motion capture device, and (iii) the infrared motion capture device.

11. The method according to claim 8, wherein the second numerical score that is determined by the data processing device for the subject comprises one or more of the following: (i) a maximum sway of the center-of-pressure of the subject, (ii) a maximum sway of the center-of-gravity of the subject, and (iii) a confidence area for a path of the center of pressure of the subject.

12. The method according to claim 8, wherein the first numerical score that is determined by the data processing device for the subject further comprises one or more of the following: (i) an eye velocity of one or more eyes of the subject, and (ii) an accuracy parameter specifying an accuracy of one or more eyes of the subject.

13. The method according to claim 8, wherein the step of assessing a performance of the subject comprises assessing the performance of the subject so as to evaluate one or more of the following medical conditions: (i) a traumatic brain injury or concussion, (ii) a neurological disorder or disease, and (iii) a muscular disorder or disease.

* * * * *